(12) United States Patent
Lu et al.

(10) Patent No.: US 10,801,879 B2
(45) Date of Patent: Oct. 13, 2020

(54) MAGNESIUM ZINC OXIDE NANOSTRUCTURE MODIFIED BIOSENSOR AND MONITORING OF RESPONSE OF CELL POPULATION TO AN AGENT USING THE SAME

(71) Applicant: Rutgers, The State University of New Jersey, New Brunswick, NJ (US)

(72) Inventors: Yicheng Lu, East Brunswick, NJ (US); Pavel I. Reyes, New York, NY (US); Steven Zheng, Watchung, NJ (US); Andrew Zheng, Watchung, NJ (US); Keyang Yang, Piscataway, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 241 days.

(21) Appl. No.: 15/927,710

(22) Filed: Mar. 21, 2018

(65) Prior Publication Data
US 2018/0209836 A1    Jul. 26, 2018

Related U.S. Application Data

(63) Continuation-in-part of application No. PCT/US2016/052961, filed on Sep. 21, 2016.
(Continued)

(51) Int. Cl.
*H01L 41/113* (2006.01)
*H01L 41/187* (2006.01)
(Continued)

(52) U.S. Cl.
CPC ............ *G01G 3/165* (2013.01); *C12M 1/34* (2013.01); *C12Q 1/025* (2013.01); *C12Q 1/04* (2013.01);
(Continued)

(58) Field of Classification Search
CPC . H01L 41/1132; H01L 41/1871; H01L 41/18; G01N 33/5008; G01N 29/022;
(Continued)

(56) References Cited

U.S. PATENT DOCUMENTS

| 5,770,373 A | 6/1998 | Britschgi et al. |
| 6,914,279 B2 * | 7/2005 | Lu ........................ C12Q 1/6825 257/252 |

(Continued)

FOREIGN PATENT DOCUMENTS

| EP | 2515111 A1 | 10/2012 |
| KR | 20130017567 | * 11/2010 |
| WO | 2005050164 A2 | 6/2005 |

OTHER PUBLICATIONS

Voiculescu, et al: "Chapter4: Acoustic Wave Based MEMS Devices, Development and Applications", Microelectromechanical Systems and Devices, Mar. 28, 2012, pp. 65-86.
(Continued)

*Primary Examiner* — Jacques M Saint Surin
(74) *Attorney, Agent, or Firm* — Fox Rothschild LLP

(57) ABSTRACT

A magnesium zinc oxide (MZO) nanostructure modified quartz crystal microbalance ($MZO_{nano}$-QCM) takes advantage of the unique sensing ability and biocompatibility of MZO-based nanostructures, and combines them with the dynamic impedance spectrum capability of the bulk acoustic wave (BAW) devices including QCM, to form a real-time, noninvasive and label-free cell monitoring biosensor, specifically detecting the susceptibility and resistance of bacterial and fungal strains and cancer cells to various antibiotic and antifungal drugs and anticancer drugs, respectively.

27 Claims, 19 Drawing Sheets

Related U.S. Application Data

(60) Provisional application No. 62/340,916, filed on May 24, 2016, provisional application No. 62/221,583, filed on Sep. 21, 2015, provisional application No. 62/291,231, filed on Feb. 4, 2016.

(51) Int. Cl.

| | |
|---|---|
| *H01L 41/18* | (2006.01) |
| *G01N 29/02* | (2006.01) |
| *G01N 29/46* | (2006.01) |
| *C12Q 1/04* | (2006.01) |
| *C12Q 1/02* | (2006.01) |
| *G01N 33/50* | (2006.01) |
| *C12M 1/34* | (2006.01) |
| *G01G 3/13* | (2006.01) |
| *G01H 11/08* | (2006.01) |
| *G01H 13/00* | (2006.01) |
| *G01N 33/483* | (2006.01) |
| *H01L 41/29* | (2013.01) |
| *G01G 3/16* | (2006.01) |
| *B82Y 15/00* | (2011.01) |

(52) U.S. Cl.
CPC ............... *G01G 3/13* (2013.01); *G01H 11/08* (2013.01); *G01H 13/00* (2013.01); *G01N 29/022* (2013.01); *G01N 29/46* (2013.01); *G01N 33/4833* (2013.01); *G01N 33/5005* (2013.01); *G01N 33/5008* (2013.01); *H01L 41/1132* (2013.01); *H01L 41/18* (2013.01); *H01L 41/1871* (2013.01); *H01L 41/29* (2013.01); *B82Y 15/00* (2013.01); *G01N 2291/0256* (2013.01)

(58) Field of Classification Search
CPC ............... G01N 29/46; G01N 33/4833; G01N 33/5005; G01N 2291/0256; C12M 1/34; C12Q 1/025; C12Q 1/04; G01G 3/13; G01G 3/165; G01H 11/08; G01H 13/00; B82Y 15/00
USPC .......................................................... 73/580
See application file for complete search history.

(56) References Cited

U.S. PATENT DOCUMENTS

| | | | |
|---|---|---|---|
| 8,377,683 B2 * | 2/2013 | Lu ........................... | B82Y 5/00 |
| | | | 119/300 |
| 10,161,898 B2 * | 12/2018 | Kinser .................... | C25D 1/006 |
| 2003/0008335 A1 | 1/2003 | Marx et al. | |
| 2003/0129307 A1 | 7/2003 | Lu et al. | |
| 2004/0150296 A1 | 8/2004 | Park et al. | |
| 2004/0222476 A1 | 11/2004 | Ahn et al. | |
| 2005/0260745 A1 | 11/2005 | Domansky et al. | |
| 2007/0210349 A1 | 9/2007 | Lu et al. | |
| 2008/0014192 A1 | 1/2008 | Poeta et al. | |
| 2008/0149840 A1 | 6/2008 | Handique et al. | |
| 2011/0196259 A1 | 8/2011 | Gianchandani et al. | |
| 2012/0051976 A1 | 3/2012 | Lu et al. | |
| 2012/0258444 A1 | 10/2012 | Therrien et al. | |
| 2013/0017567 A1 * | 1/2013 | Lu ........................... | B82Y 5/00 |
| | | | 435/29 |
| 2013/0063858 A1 | 3/2013 | Dogan et al. | |
| 2014/0199757 A1 | 7/2014 | Kim et al. | |

OTHER PUBLICATIONS

Zhang, et al: "A Novel Sensitive Cell-Based Love Wave Biosensor for Marine Toxin Detection", Biosensors and Bioelectronics, 2016, vol. 77, pp. 573-579.

* cited by examiner

E. coli culture on ZnO after 90 minute incubation

E. coli culture on MZO after 90 minute incubation

MAGNESIUM ZINC OXIDE NANOSTRUCTURE MODIFIED BIOSENSOR AND MONITORING OF RESPONSE OF CELL POPULATION TO AN AGENT USING THE SAME

CROSS-REFERENCE TO RELATED APPLICATIONS

This application is a Continuation-in-part application of International patent application serial No. PCT/US16/52961, filed on Sep. 21, 2016, which claims priority under 35 U.S.C. § 119(e) to U.S. Provisional Patent Application Ser. No. 62/221,583, filed on Sep. 21, 2015, U.S. Provisional Patent Application Ser. No. 62/291,231, filed on Feb. 4, 2016, and U.S. Provisional Patent Application Ser. No. 62/340,916, filed on May 24, 2016, all of which are incorporated herein by reference.

STATEMENT REGARDING FEDERALLY SPONSORED RESEARCH OR DEVELOPMENT

This invention was made with government support under Grant No. NSF-1264508 awarded by the National Science Foundation (NSF) Chemical, Bioengineering, Environmental, and Transport Systems (CBET) Division. The government has certain rights in the invention.

BACKGROUND

The present invention relates to the biosensors and particularly to magnesium zinc oxide (MZO) nanostructure-modified biosensors and applications of the biosensors including monitoring of response of cell population to an agent.

According to World Health Organization, antimicrobial resistance (AMR) has become a major global health concern that it threatens to become the next "Pandemic". There is an urgent need for sensitive diagnostic surveillance tools. For example, approximately 3.5% of new and 20.5% of previously-treated tuberculosis (TB) cases have multi-drug resistant (MDR) TB. Due to the lack of effective drug-susceptibility test (DST), only 20% of MDR-TB cases receive proper treatment, contributing to onward transmission of MDR-TB and unnecessary suffering and death. Because of the slow growth of M. tuberculosis bacteria, the standard agar/liquid methods typically require four to eight weeks to obtain results. Newer DST techniques have improved the reliability and speed of testing, but still suffer distinct disadvantages that limit broad applications. Phenotypic testing methods take an average of four weeks and the procedures must be carried out by highly trained technical personnel. Molecular methods such as polymerase chain reaction (PCR) detection of drug-resistant mutations can reduce the detection time, but they are pathogen-specific, and cannot reliably detect all existing mutations or new mechanisms. Moreover, they are not suitable for DST. There is an urgent need for new technologies that rapidly and economically detect AMR and identify appropriate antibiotic for treatment.

According to statistics, with an overall aging population and life style changes in developing countries, cancer has become a global epidemic. According to World Health Organization (WHO), there were 14.1 million new cancer cases and 8.2 million cancer-related deaths worldwide in 2012. The number of new cancer cases is expected to increase to 24 million by 2035. The high cancer mortality rate is due in a major part to the low response rate to drug therapy. It is increasingly recognized that human cancers are highly variable both genetically and epigenetically even within the same type of tumors, limiting successful drug therapy. Examples of molecular events that restrict therapeutic efficacy include drug transport, drug binding site mutations, activation of survival mechanisms, and activation of alternative and feedback pathways to the therapeutic targets. Because of these diverse mechanisms, individual tumors of the same type often have a very different response to a particular drug treatment. Even for targeted anticancer drugs such as small molecule epidermal growth factor receptor (EGFR) inhibitors in lung cancer, for which surrogate biomarkers are available to predict treatment outcome, other variable factors can limit treatment outcomes. As a result, the typical response rate of a given anticancer drug in a general cancer patient population is less than 20%. There is an urgent need to develop adequate new screening methods to predict individualized responses.

Recent advances in next-generation sequencing technology have led to the precision medicine initiative that uses cancer genomic information to guide treatment plans, which has achieved some success. However, tumors, especially late stage cancers often accumulate a large burden of mutations and epigenetic alterations, making it very difficult to determine the main cancer-driving events and design successful therapies. Therefore, new and complementary technologies are still urgently needed to guide clinicians to determine the most appropriate treatment plans for individual cancer patients. A number of technologies have been developed over the years to facilitate in vitro testing of anticancer drug responses. The well recognized methods include establishment of cancer cell lines, cancer organoids/spheroids, and patient-derived xenograft (PDX) tumors in immunodeficient mice. These new resources have greatly enhanced the ability to understand molecular mechanisms of drug sensitivity and resistance. However, these tumor models take lengthy time to establish, typically months and up-to-a year, before they are suitable for analysis of therapeutic responses. Moreover, large tumor samples are required. Currently, they remain mostly for drug discovery and research purposes. Thus, there is a great need for new technologies that can be used to directly determine treatment outcome with small fresh biopsy of primary tumors. Our biosensor has the promise to analyze anticancer drug activity within minutes to hours, making it a practical solution for predicting treatment outcomes for individual cancer patients.

This document describes devices, systems and methods that may address at least some of the issues described above and/or other issues.

SUMMARY

Combining advantages of magnesium-doped zinc oxide (MZO) nanostructures ($MZO_{nano}$) with the dynamic impedance spectrum capability of a bulk acoustic wave (BAW) device such as a quartz crystal microbalance (QCM) makes $MZO_{nano}$-QCM a highly-sensitive biosensor well-suited for monitoring dynamic detection of response of a cell population to an agent, including antimicrobial Resistance (AMR) effects. MZO nanostructure modified quartz crystal microbalance ($MZO_{nano}$-QCM) takes advantage of the unique sensing ability and biocompatibility of MZO-based nanostructures, and combine them with the dynamic impedance spectrum capability of the bulk acoustic wave (BAW) devices including QCM to form a real-time, noninvasive and label-free cell monitoring biosensor, which is specifically suitable for detecting the susceptibility and resistance of bacterial and fungal strains and cancer cells to various antibiotic and antifungal drugs and anticancer drugs, respectively.

The multifunctional properties of MZO films and nanostructures, serving as both the cell interface and the sensitivity-enhancing material, can be utilized to form $MZO_{nano}$-QCM bacterial, fungal and cancer cell monitoring sensors. In addition to the increased effective sensing surface provided by MZO nanostructures, the sensitivity of the biosensor is greatly enhanced through the control and optimization of (i) surface morphology, (ii) surface wettability of the MZO nanostructures and (iii) toxicity profile of the MZO nanostructures. This enhanced sensitivity allows simultaneous multiple parameters to be output in a single measurement and enables non-invasive measurement of a change in the biophysical properties of a cell population in response to an agent. The biophysical properties, mainly viscoelastic transitions and mass accumulation (mass-loading) related to cell activity (growth and viability), can be continuously monitored in real-time through the specific time-evolving sensor spectral signatures (i.e., spectral shape, Nyquist-map rotational characteristics, and frequency peak shifting). The MZO nanostructure deposited on the surface of top electrode of the BAW device does not change the overall size of the BAW device, thereby resulting in a portable and cost effective design.

In one embodiment, a MZO-BAW sensor device for monitoring growth of a cell population includes a piezoelectric layer sandwiched between a top and bottom electrodes, where the top electrode and bottom electrodes can be metal, alloy or transparent conductive oxide, and deposited and patterned on the piezoelectric layer. The sensor device also includes $Mg_xZn_{1-x}O$ (MZO)-based nanostructures deposited and patterned on the top electrode of sensor device. The Mg composition x in MZO (the percentage composition of Mg in MZO) is in the range of $0<x<0.2$. The Mg composition x can also be between 0.01 and 0.05 ($0.01<x<0.05$). Alternatively, and/or additionally, the Mg composition x in MZO is in the range from 0.04 to 0.05 (4-5%), or is 0.03 (3%).

MZO-based nanostructures include a surface morphology that can be selected from substantially flat surface, rough surface, nanotip or rod arrays having sharp tips, and nanotip or rod arrays rounded tops.

In some other embodiments, the nanostructure deposited and patterned on a top surface of the top electrode of the BAW device is comprised at least one of: ZnO-based nanostructures, $SiO_2$-base nanostructures, $TiO_2$-based nanostructures and $Si_xN_y$-based nanostructure.

The MZO-BAW sensor device may be either a quartz crystal microbalance (QCM) sensor or a thin film balk acoustic wave resonator (TFBAR) sensor. In an example, the MZO-BAW sensor is QCM-based ($MZO_{nano}$-QCM), in which the piezoelectric layer includes a QCM and the MZO nanostructures are deposited on the surface of the top electrode of the sensor device. In another example, the MZO-BAW sensor is TFBAR-based ($MZO_{nano}$-TFBAR), in which the piezoelectric layer includes a TFBAR and the MZO nanostructures are deposited on the surface of the top electrode. The TFBAR sensor is capable of operating at a higher frequency (multi-GHz) than that of QCM sensor; thus offers higher sensitivity.

In one embodiment, a method of monitoring the response of a cell population to an agent includes: providing a MZO-BAW sensor device as disclosed in this document. In the MZO-BAW sensor device, the $Mg_xZn_{1-x}O$ (MZO)-based nanostructures that are deposited and patterned on the top electrode, the Mg composition x in MZO is in the range from $0<x<0.2$. The Mg composition x can also be between 0.01 and 0.05 ($0.01<x<0.05$). Alternatively, and/or additionally, the Mg composition x in MZO is in the range from 0.04 to 0.05, i.e. 4-5%, or is 0.03 (3%).

The method also includes culturing a cell population in contact with the nanostructures; generating time-frequency signals in the sensor device; receiving output signals corresponding to frequency response spectra of the $MZO_{nano}$-BAW sensor device; contacting the cell population with an agent; continuing to culture the cell population, generate the time-frequency signals and receive the output signals corresponding to frequency response spectra; dynamically and continuously monitoring the changes in the output signals by measuring the frequency response spectra; and extracting data from the output signals, and analyzing the data to determine a response of the cell population to the agent.

In extracting data, the method may extract data from the time-frequency output signals, such as spectral shape evolution data, peak frequency shift data, motional resistance data, motional induction data, and/or Nyquist map rotation data. The response and the extracted data are indicative of a change in viscoelastic property and/or mass-loading of the cell onto the nanostructures. The method of extracting data may use a data simulation and modeling technique based upon a Butterworth-Van-Dyke (BVD) lumped-parameter model and a multi-layer transmission line signal propagation model.

The response of the cell to the agent reflects a change in the viscoelastic property and/or in the mass-loading of the cell onto the nanostructures. And the method may further include comparing the extracted data with a reference to determine the anti-microbial effect of the agent and/or anti-biotic resistance of the cell to the agent. The method may also alternatively and/or additionally include comparing the data with a reference to determine the anti-cancer effect of the agent on the cell.

The cell to be cultured on the surface of the MZO-based nanostructure can be a bacterial cell, a fungal cell, a parasite cell, or a freshly isolated cancer cell cultured directly on the surface of the MZO-based nanostructure. For example, the cell is a pathogenic bacterial cell and the agent is an anti-pathogenic bacterial agent. In an another example, the cell is a fungal cell and the agent is an anti-fungal agent. Examples of fungal cells include *Candida albicans* and *Cryptococcus neoformans*. In another example, the cell is a parasite cell and the agent is an anti-parasite agent. In another example, the cell is a cancer cell, and the agent is an anti-cancer agent. The method may dispose the cell to be cultured to be in indirect contact with the MZO sensing surface.

MZO-based nanostructures may be in direct or indirect contact with the top electrode of the BAW device. When in indirect contact, a thin non-conductive layer (such as $SiO_2$) or a thin conductive layer (such as Ga-doped ZnO-GZO) may be deposited on the top electrode, and the MZO nanostructures are deposited on the top of $SiO_2$ or GZO thin layer.

The top and bottom electrodes of the BAW device can be a metal (Au, Cu, etc), an alloy, a transparent conductive oxide (TCO), such as Ga-doped ZnO (GZO), Al-doped ZnO (AZO), or their combinations. When TCO electrodes are used, the whole device becomes a transparent BAW sensor device. The surface morphology of the nanostructures is controlled and is selected from substantially flat surface, rough surface, or nanostructured surfaces with nanotip arrays having sharp tip-ends, or nanorod arrays having rounded ends.

In one embodiment, a method of monitoring the growth of a cell population includes providing a MZO-BAW sensor device that is disclosed in various embodiments in this document, in which $Mg_xZn_{1-x}O$ (MZO)-based nanostructures deposited and patterned on a top electrode of the BAW device, wherein $0<x<0.2$. The method further includes culturing a cell population in contact with said nanostructures; receiving output signals corresponding to frequency response spectra of the $MZO_{nano}$-BAW sensor device; extracting data from the output signals indicative of a change in the viscoelastic property and/or mass-loading of the cells of the cell population, and analyzing the data using simulation and modeling.

The method further includes collecting samples from a subject suspected of carrying bacterial pathogens. For example, the sample is collected from food, agricultural product, water source, and environment pollutant.

In one embodiment, a method of manufacturing a MZO nanostructure-modified bulk acoustic wave ($MZO_{nano}$-BAW) sensor device includes providing a bulk acoustic wave (BAW) device. The BAW is the QCM or the TFBAR. The method further deposits $Mg_xZn_{1-x}O$ (MZO)-based nanostructures on a surface of the top electrode of the BAW device, wherein the percentage composition (x) of Mg in MZO is in the range of $0<x<0.2$.

The method also includes selecting the percentage composition (x) of Mg in MZO in a proper range so that certain characteristics are satisfied. For example, the percentage composition (x) is selected to provide a proper surface morphology to enhance the bonding with the selected bio species. In another example, the percentage composition (x) of Mg in MZO is selected to provide a proper wettability to enhance the bonding with the selected biospecies and to reduce the amount of biospecies needed for sensing. In another example, the percentage composition (x) of Mg in MZO is selected to reduce toxicity. In another example, the percentage composition (x) of Mg in MZO is selected to expand the pH range over which the nanostructures can be sustained during the sensing process.

The wettability ranges from super hydrophobicity to super hydrophilicity. The wettability status can be controlled in both directions by adjusting the oxygen vacancy density at the MZO surface during the growth or post growth to control the surface wettability of the MZO. the Mg composition x can be in the range of $0.01<x<0.05$.

The percentage composition (x) of Mg in $Mg_xZn_{1-x}O$ (MZO) is selected to provide proper wettability to enhance the attachment and non-toxicity to bio-samples for biosensing, and large pH range for stability of the MZO nanostructures during the sensing process.

The sensor device can also be configured to operate in dual mode operation: producing an acoustic signal in acoustic admittance, and an optical signal in fluorescence, simultaneously or separately for biosensing. The biosensing can also be used for monitoring antimicrobial resistance (AMR).

The $MZO_{nano}$-BAW sensor can also be deployed inside a plurality of cell-growth wells. The sensor can further contain an interface capable of connecting the sensor to a mobile and wireless device for data transfer, storage, processing and/or display.

BRIEF DESCRIPTION OF THE DRAWINGS

FIGS. 4A and 4C show the antibiotic efficacy of ampicillin and tetracycline on E. coli, while FIGS. 4B and 4D show the detection of antimicrobial resistance (AMR) of resistant strain of E. coli to ampicillin and tetracycline.

FIGS. 6A and 6B show the detection of fungicidal response to amphotericin and fungi-static response to miconazole according to some embodiments. FIG. 6C shows the detection of normal (no-drug) growth condition of yeast according to some embodiments. FIG. 6D illustrates the detection of antifungal drug effects on S. cerevisiae (yeast) using the spectrophotometry ($OD_{600}$).

FIG. 15(a) illustrates the frequency shift. FIG. 15(b) illustrates the motional resistance, which is directly calculated using the Butterworth VanDyck Model (BVD) is indicative of cell stiffness and elasticity (viscoelastic transitions of the cell culture).

DETAILED DESCRIPTION

Figure 1A:
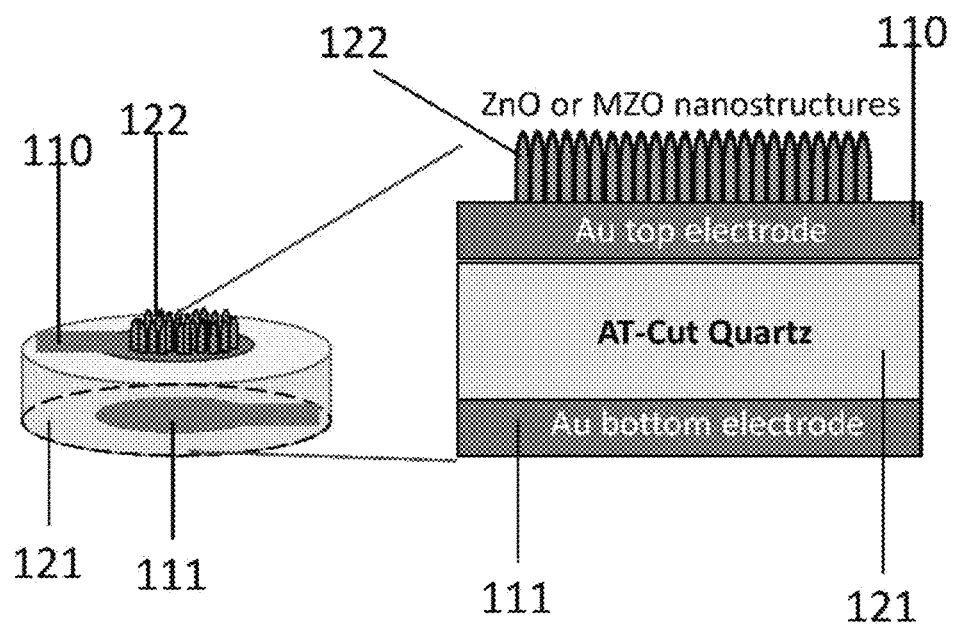
FIG. 1A illustrates a magnesium zinc oxide (MZO) nanostructure-modified quartz crystal microbalance ($MZO_{nano}$-QCM) biosensor according to an embodiment.

Various embodiments of the invention relate to design, manufacturing of magnesium zinc oxide (MZO) nanostructure-modified biosensors, and detection and monitoring of cells using MZO nanostructure-modified biosensors. In particular, system and detection methods are provided to automatically and continuously detect the AMR effects by monitoring the changes in viscoelastic properties and mass of bacterial and fungal cells cultured on the MZO nano-sensing surface through measuring and analyzing the acoustic frequency responses from the $MZO_{nano}$-QCM. These biophysical measurements provide information on microbes and antimicrobial efficacy and resistance due to drug effects through detection of the alteration of bacterial and fungal cell physiology such as growth status and viability.

Some of the advantages of various embodiments in this patent document include: (1) high sensitivity (for example: $MZO_{nano}$-QCM ~0.3 ug/kHz, while for $MZO_{nano}$-TFBAR, 5 ng/kHz); (2) fast detection speed for monitoring the AMR effects (for example, in E. coli, only taking 30 min vs 1.5 days (70×), for yeast, 60 min vs 2.5 days (60×) in comparison with use of the conventional technology; (3) label-free, and continuous monitoring of AMR effects under normal physiological conditions; (4) real time automated and quantitative data collection; (5) small sample quantity (nano- to micro-liter scale); (6) dynamic and continuous detection of AMR effects through characterization of biophysical properties of the cells in the specific spectral signatures of the bulk acoustic wave (BAW); (7) wireless data collection through mobile devices such as cell phone in the same frequency domain; (8) high throughput using multiplexing and high content arraying when the device uses the thin film bulk acoustic resonator (TFBAR) configuration; (9) small size, especially for the device using the TFBAR configuration, which is particularly useful for portable and mobile applications; and (10) low-cost.

These features make the systems and methods disclosed in this patent document suitable for broad applications such as AMR, providing a diagnostic tool for monitoring antibiotic resistance and for screening drugs that work against resistant strains, and a research tool for new antimicrobial drug discovery, and a diagnostic tool for detecting anticancer drug responses for personalized cancer treatment and cancer drug discovery. These applications may be used in a doctor's office, by a patient's bedside, on a mobile app or at research centers.

Throughout this patent document, various publications are referenced. The disclosures of these publications in their entireties are hereby incorporated by reference into this application in order to more fully describe the state of the art to which the disclosed matter pertains. While the following text may reference or exemplify specific components of a device or a method of utilizing the device, it is not intended to limit the scope of the invention to such particular references or examples. Various modifications may be made by those skilled in the art, in view of practical and economic considerations, such as the composition and morphology of the nanostructure and the condition of the culture medium.

The articles "a" and "an" as used herein refers to "one or more" or "at least one," unless otherwise indicated. That is, reference to any element or component of the present invention by the indefinite article "a" or "an" does not exclude the possibility that more than one element or component is present.

The term "about" as used herein refers to the referenced numeric indication plus or minus 10% of that referenced numeric indication.

The term "cell" as used herein refers to any type of living organism that may proliferate under suitable conditions. Non-limiting examples include mammalian cells, bacteria, fungi, yeast, and other parasitic pathogens. Other examples of the cells of interest include those that proliferate by cell division and those that grow in a non-dividing manner such as differentiated cells, senescent cells.

The term "agent" as used herein refers to any substance that may exhibit an effect on the growth of a cell. Examples include a compound, a protein or a natural product extract, drug compound.

The term "response" as used herein refers to a change in one or more biophysical properties of a cell or cell population, such as mass, viscosity, elasticity, etc. as a result of cell growth or lysis.

The term "biosensor" or "biosensor device" as used herein refers to a MZO nanostructure modified bulk acoustic wave device ($MZO_{nano}$-BAW) device, unless other indicated. The $MZO_{nano}$-BAW is the MZO nanostructure-modified QCM ($MZO_{nano}$-QCM); the $MZO_{nano}$-BAW is the MZO nanostructure-modified thin film bulk acoustic wave resonator ($MZO_{nano}$-TFBAR).

In an illustrated embodiment, with reference to FIG. 1A, a MZO nanostructure modified bulk acoustic wave (BAW) sensor device ($MZO_{nano}$-BAW) may include a top electrode 110 and a bottom electrode 111, and a piezoelectric layer 121 sandwiched between the top electrode and bottom electrode. The sensor device also includes nanostructures 122 (a schematic diagram is shown) such as $Mg_xZn_{1-x}O$ (MZO)-based nanostructures deposited and patterned over the top electrode. The percentage composition (x) is in the range of 0<x<0.2 and x is selected to provide at least one predetermined characteristic selected from wettability, non-toxicity, and pH stability of the MZO nanostructures. In a non-limiting example, with reference to FIG. 1B, MZO nanostructures 130 (a scanning electron microscope (SEM) picture is shown) are deposited on the top of Au electrode surface.

Returning to FIG. 1A, the bottom electrode 111 may include a conductive film deposited and patterned beneath the piezoelectric layer 121; the top electrode 110 may include a metal electrode deposited and patterned on the piezoelectric layer 121; and $Mg_xZn_{1-x}O$-based nano-structures 122 are deposited and patterned on the top surface of the top electrode, where 0<x<0.20.

The wettability status (from super hydrophobicity to super hydrophilicity, or vice versa) of the MZO nanostructures 122 can be controlled by adjusting the oxygen vacancy density at the MZO surface during growth or post growth. Wettability can be enhanced, for example, from hydrophilicity to super hydrophilicity, especially for the MZO nanostructures with tip-type of sharp surface morphology. The hydrophilicity of the MZO-based nanostructures can reduce the sensor's liquid sample consumption and enhance the sensitivity significantly. Optimization of the wettability leads to enhanced binding with the specific biospecies or cells.

In the illustrated embodiment, the percentage composition of Mg in MZO (i.e. x in $Mg_xZn_{1-x}O$) ranges between 0 and 20% (0<x<0.2). However, it should be noted that such range is merely illustrative for achieving a desired performance. The exact x value is critical to obtain the high sensitivity and selectivity of the $MZO_{nano}$-BAW sensor through the control of a Mg composition during the deposition of MZO nanostructure.

In comparison with pure ZnO (x=0), the addition of a small amount of Mg (for example 5%) in the $Mg_xZn_{1-x}O$-based nanostructures enables an increase in the range of sample pH values that the nanostructures can withstand, and therefore improves the stability and durability of the $MZO_{nano}$-BAW sensors during the measurement and manufacturing processes.

The amount of Mg in MZO directly impacts important characteristics of the nanostructure, including wettability, surface morphology, and the stability and biocompatibility of the MZO-nanostructures under various pH conditions. Further, a suitable range of Mg also leads to low-level toxicity or non-toxicity of the MZO nanostructure; thus enhances the biocompatibility of the $MZO_{nano}$-BAW sensors. In one example, the range of x can be any grouping of values greater than 0 and less than 0.2, however some preferred ranges are about 0.01 to about 0.05 or even 0.02 to about 0.04 or about 0.03 or about 0.04 to 0.05. Therefore, the Mg composition in $Mg_xZn_{1-x}O$ (MZO) needs to be adjusted and optimized depending on the factors such as the nature, the property, the size of the sample, the pH value of the cell culture, the temperature, the stability, and the desired toxicity (or non-toxicity) level.

The MZO-based nanostructures disclosed and shown in FIG. 1A can be grown on a substrate by metal-organic chemical vapor deposition (MOCVD) and other chemical or physical deposition technologies, then patterned by photolithography and etching process. Undoped ZnO and its nanostructures show n-type semiconducting behaviors. Magnesium (Mg) can be introduced in-situ during the growth of ZnO to form the ternary compound MgxZn1–xO (0<x<0.2) i.e. MZO to modify the physical and chemical properties of the ZnO-based nanostructures.

MZO, like the pure binary ZnO, can be made multifunctional through doping to be suitable for various sensing applications. For example, the dopants of group III-donors like Al and Ga significantly enhance the electrical conductivity; transitional metal (TM) dopants like Fe and Mn make it ferromagnetic; compensational dopants like Cu and Ni make it piezoelectric.

MZO can be grown with various morphologies such as thin films and nanotips and nanorods on a large number of substrates including insulators, such as glass, quartz and Al2O3; semiconductors, such as Si, GaAs, GaN and SiC; electrodes, such as metals and transparent conductive oxides (TCO); and also on the flexible substrates such as polymers. In an example, MZO with suitable surface morphology is directly deposited on the Au top-electrode of the QCM and TFBAR.

As used herein with respect to surface morphology of the nanostructured MZO, the phrase "substantially flat" is defined as a MZO film with the surface roughness (rms) of ~1.5 nm. "Rough" is defined as a MZO film with the surface roughness (rms) of ~7.5 nm and is characterized by irregularities, protuberances, and/or ridges. "Sharply uneven" is defined as a MZO film with closely packed nanotip/nanorods arrays and the diameter of the tip top ranging between 5-100 nm.

Controlling the morphology of the MZO-based nanostructure surfaces (e.g. thin film or substantially flat, rough surface, and sharp tips) can enhance the binding of the nanostructure with certain biological cells (e.g., the bacterial and fungal cells for AMR tests), which allows monitoring the susceptibility and resistance of bacterial and fungal strains to various antibiotic and antifungal drugs. For example, when the cells being monitored are mammalian, a BAW sensor device with substantially flat nanotip structures can be used. When the cells being monitored are fungal, a BAW sensor device with rough nanotip structures is suitable. When the cells being monitored are bacterial or viral, a BAW sensor device with rough nanotip structures provides the describable sensitivity. Nanostructured MZO can also be used to bind with bacterial and viral cultures for reaction with enzymes and antibodies for applications in immunosensing. Manipulation of the morphology of the MZO nanoparticles also serves to maximize the sensitivity for particular cells and analytes.

Both ZnO (x=0) nanostructure-modified BAW devices ($ZnO_{nano}$-BAW) and the MZO (0<x<0.2) nanostructure-modified BAW devices ($MZO_{nano}$-BAW) have the advantages over the regular BAW devices without integrated nanostructures. For example, some advantages of QCM devices include: (i) the nanostructure-modified QCM devices have larger effective sensing surface areas; (ii) the wettability and surface morphology can be controlled to enhance the binding with the proper cells; and (iii) the other chemical and physical properties such as electrical conductivity can be controlled through doping. These advantages enable both $ZnO_{nano}$-QCM and $MZO_{nano}$-QCM to have much higher sensitivity and consume much less liquid biosample amount than the regular QCM devices.

Figure 2A:
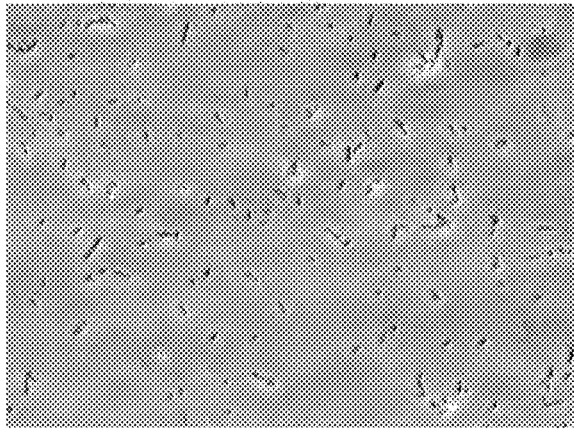
FIGS. 2A and 2B illustrate decreased cell death of E. coli on MZO according to an embodiment (x=0.03) as compared to ZnO thereby increasing the MZO-based biosensor's sensitivity and biocompatibility.
Figure 2B:
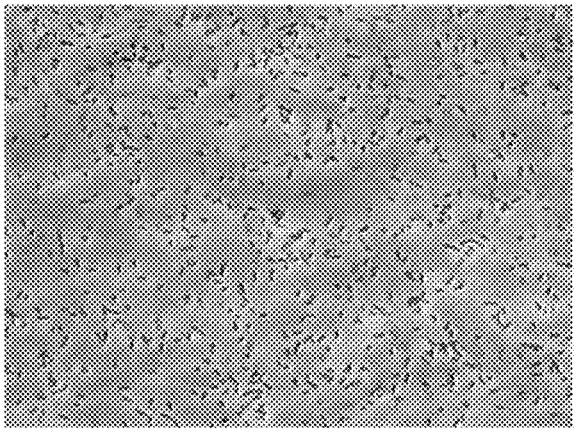
Figure 2C:
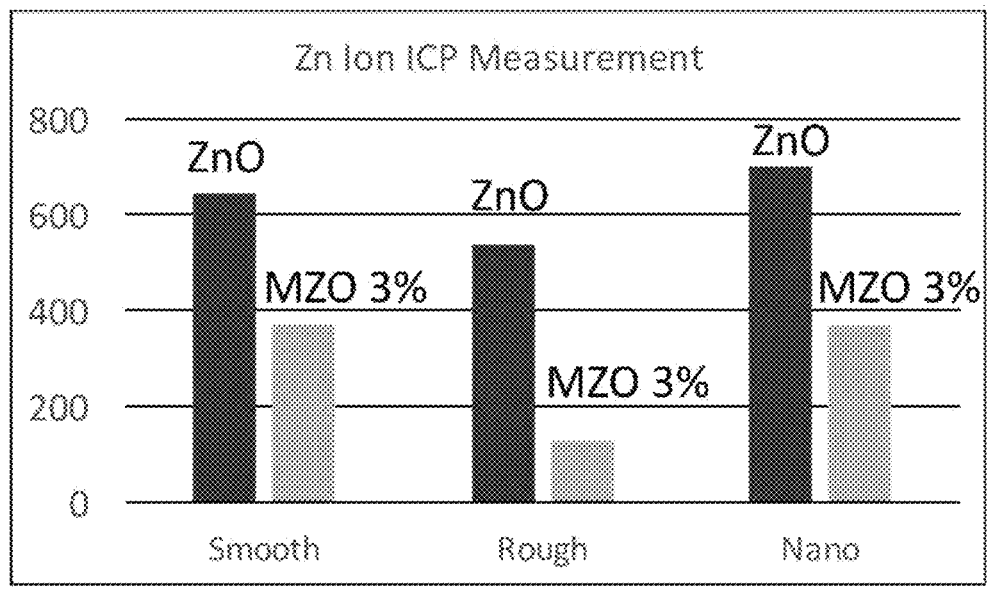
FIG. 2C illustrates the verification of the increased biocompatibility of MZO to bacterial culture through the demonstration of 5× lower concentration of $Zn^{2+}$ ions in cell culture medium which is the main ionic species causing toxicity to bacterial cultures.

In comparing $MZO_{nano}$-QCM with $ZnO_{nano}$-QCM, the $MZO_{nano}$-QCM show much higher sensitivity than the $ZnO_{nano}$-QCM (for example in E-coli, 5× high). $MZO_{nano}$-QCM also shows significantly lower detection limits. For example, the detection limit of 0.1-0.9 ng (100-900 E. coli cells) is 10-fold lower than the 1-9 ng detection limit for $ZnO_{nano}$-QCM (E. coli has an average mass of ~1 pg). Some reasons for the advantages of the MZO nanostructure-based biosensor device over its ZnO nanostructure-based counterpart are (i) MZO is more stable than pure ZnO under wide pH-value ranges and different temperatures; thus, the MZO devices offer much longer shelf life and better functionality under different working conditions; (ii) The toxicity level of MZO nanostructures is much lower than that in ZnO based counterpart due to significantly reduced Zn ion release from MZO, as shown in FIG. 2C.

In another illustrated embodiment, a method for fabricating the MZO-BAW sensor device may use the procedure disclosed in the U.S. Pat. No. 8,377,683, the entire disclosure of which is hereby incorporated by reference. In addition, in manufacturing, the percentage composition of Mg in MZO (i.e. x in $Mg_xZn_{1-x}O$) may vary (0<x<0.2), as described above, depending on the specific needs for biodetection (such as the size of the biomolecules) and the sensing conditions (such as pH and temperature).

The piezoelectric material used in the BAW can be, but is not limited to, quartz, $LiNbO_3$, $LiTaO_3$, ZnO and the like. The metal electrodes are deposited and patterned using the standard microelectronic processing techniques. The MZO-based nanostructure modified BAW ($MZO_{nano}$-BAW) sensor operates similarly to a BAW resonator device. The BAW resonator will resonate at a specific frequency determined by the piezoelectric material properties and thickness. When bonding of the target occurs on the MZO-based nanostructures, mass-loading results with a shift in the resonance frequency of the BAW device, directly proportional to the amount of target material bonded to the MZO-based nanostructures.

In some other embodiments, the nanostructure deposited and patterned on a top surface of the top electrode of the BAW device may be comprised at least one of: ZnO-based nanostructures, $SiO_2$-base nanostructures, $TiO_2$-based nanostructures and $Si_xN_y$-based nanostructure.

The MZO nanostructures can be incorporated into a BAW device, including the regular QCM to form the $MZO_{nano}$-QCM. The MZO-based nanostructures can also be incorporated into a thin film bulk acoustic resonator to form the $MZO_{nano}$-TFBAR. TFBAR consists of a piezoelectric film sandwiched between top and bottom electrodes. The TFBAR can operate at much higher frequencies. It has many advantages, such as small size, low insertion loss and lower power consumption. In addition, TFBAR sensors can be readily integrated into arrays. The TFBAR sensors can be integrated with other Si-based electronic components on the same substrate and compatible with small-size microwave aerials, and hence can be used for wireless distance probing.

In another illustrated embodiment, a monitoring system may include the sensor device disclosed in FIG. 1A. The system may also include a source for generating time-frequency signals by inducing oscillations in the piezoelectric layer of the BAW sensor device, using conventional means, and a real time signal analyzer system communicatively coupled to the sensor device. The real time signal analyzer system is configured to measure spectral responses (for example, the magnitude, phase, and spectrum shape, etc.) of the time-frequency signals. The monitoring system may also include an incubator with $CO_2$ flow; a temperature controller; and one cell-growth well deployed inside the incubator.

In the monitoring system, the $MZO_{nano}$-BAW sensor can be $MZO_{nano}$-QCM and $MZO_{nano}$-TFBAR. The monitoring system may additionally include an incubator and multiple cell-growth wells deployed inside the incubator. Two or more cell-growth wells may each have a $MZO_{nano}$-BAW sensor deployed therein. This configuration further expands the scope of the detection. For example, multiple compounds can be studied in parallel against the same cell or target. Alternatively, the same compound can be screened against multiple targets at the same time. Further, multiple $MZO_{nano}$-TFBAR sensor modules can be arrayed and integrated on the same chip, enabling parallel detection of different antimicrobial drugs.

Because output signals from the $MZO_{nano}$-BAW sensors are in frequency domain, the monitoring system may additionally include an interface to communicatively connect the sensors to wireless mobile devices (e.g. iPhone, iPad) that receive and process signals and transmit data remotely to processing or storage facilities such as hospitals and health centers.

The monitoring system may also be configured to operate in dual mode operation: producing an acoustic signal in acoustic admittance and an optical signal in fluorescence simultaneously or separately for monitoring antimicrobial resistance (AMR).

The $MZO_{nano}$-BAW sensors can be bio-functionalized to directly and selectively detect the presence and/or growth of bacterial or fungal pathogens in patient samples, water supplies, food, and agricultural products, pollutants, and environmental sources. The sensors, methods and monitoring systems thus find applications in various fields including food and agricultural product safety and environment monitoring. The bio-functionalized $MZO_{nano}$-BAW biosensors can also be used to directly and selectively detect cancer cells and anti-cancer drug response in patient samples for clinical application and personal health during chemotherapy.

Figure 3:
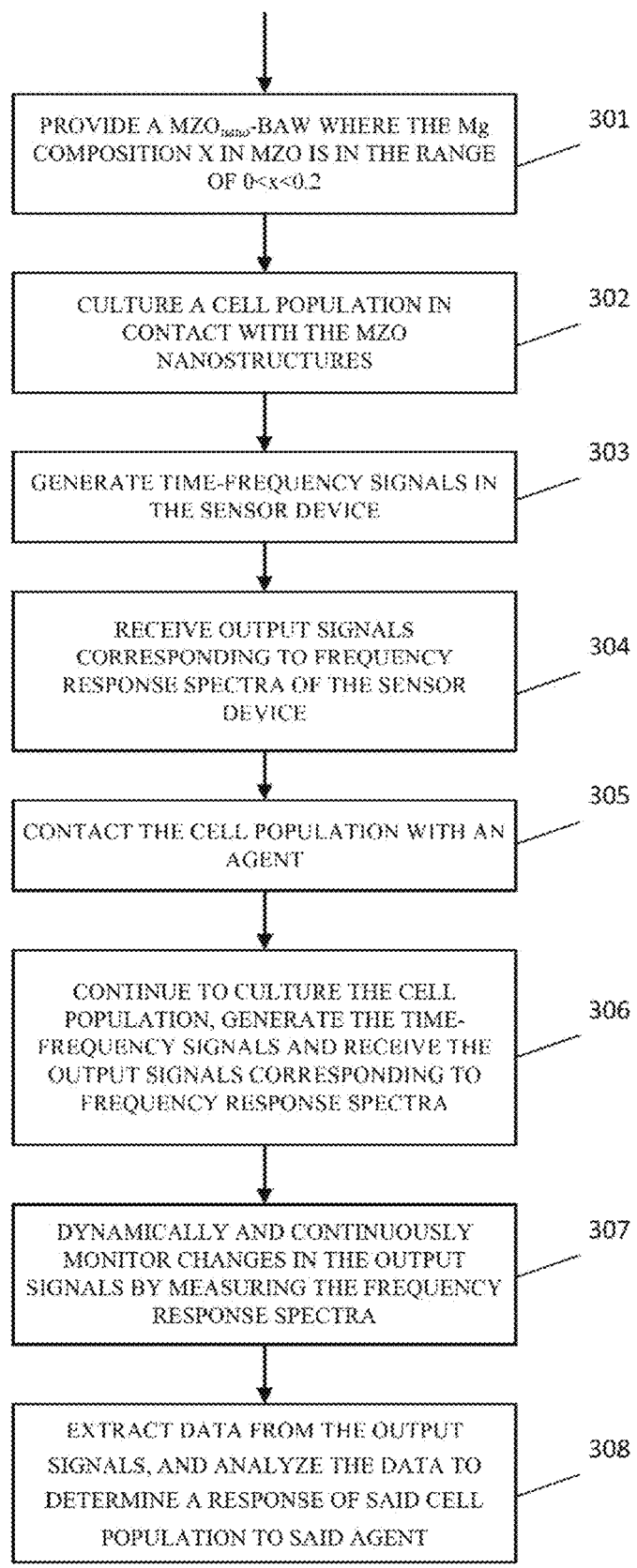
FIG. 3 illustrates a diagram of a method of monitoring response of a cell population to an agent according to an embodiment.

In another illustrated embodiment, with reference to FIG. 3, a method using a $MZO_{nano}$-BAW sensor and a monitoring system is provided for dynamically monitoring the changes in viscoelastic properties and mass of the cells cultured on the MZO nano-sensing surface through measuring and analyzing the acoustic frequency responses. The method may include: providing a magnesium-doped zinc oxide (MZO) nanostructures ($MZO_{nano}$) modified bulk acoustic wave (BAW) sensor device ($MZO_{nano}$-BAW) 301 disclosed in embodiments in FIG. 1A, where the Mg composition x in MZO is in the range of $0<x<0.2$. The method further includes culturing a cell population in contact with the MZO nanostructures 302; generating time-frequency signals in the sensor device 303, receiving output signals corresponding to frequency response spectra of the $MZO_{nano}$-BAW sensor device 304; contacting the cell population with an agent 305; continuing to culture the cell population, generate the time-frequency signals and receive the output signals corresponding to frequency response spectra 306; dynamically and continuously monitoring changes in the output signals by measuring the frequency response spectra 307; and extracting data from the output signals and analyzing the data to determine a response of said cell population to said agent 308.

In extracting data from the output signals 308, the method may extract data such as spectral shape evolution data, peak frequency shift data, Nyquist map rotation data, motional resistance data, and/or motional induction data. The data analysis, which is based on the Butterworth-Van-Dyke (BVD) lumped-parameter model and the multi-layer acoustic wave transmission line simulation, links the BAW frequency response to the cell response such as changes in the viscoelastic property and/or mass of the cell. The data analysis can thus provide the antimicrobial efficacy and resistance (AMR) information. Dynamic and continuous monitoring and analysis can also be achieved.

The method may further include comparing the extracted data with a reference to determine, for example, the anti-cancer effect or the anti-microbial effect of the agent and/or antibiotic resistance of the cell to the agent. The reference can be control data from a cell untreated with the agent or any relevant statistics. Multiple sensors can be incorporated in one platform in high throughput monitoring and diagnostics. The method and monitoring system disclosed in various illustrated embodiments in this patent document thus allow for efficient detection of resistance to anti-cancer or anti-pathogenic fungal/bacterial agents that can serve as a rapid and high throughput method or assay in drug discovery and development.

Non-limiting examples of cells to be monitored include bacterial, fungal and parasitic pathogens. Additional examples include mammalian cells such as primary cancer cells isolated from a cancer patient. The cells can be collected from patient samples, water supplies, food, and agricultural products, and environmental sources.

To maximize the sensitivity and efficiency of the detection process, different surface morphologies described above can be employed for different targets. For example, rough films are used for bacteria and substantially flatter nanostructures are used for mammalian cells.

The cell population can be cultured directly or indirectly on a surface of the MZO-based nanostructure. For example, the cells are cultured on a surface of the MZO-based nanostructure and in direct contact with the MZO sensing surface. In another example, the cells are in indirect contact with the MZO sensing surface via a suitable medium such as antibodies.

AMR for TB is a major global health issue and AMR detection in these organisms is particularly challenging due to their very slow growth. Methods using the monitoring system described in various embodiments disclosed in this document can be used to detect AMR to compounds or drugs (e.g. methicillin, amphotericin, etc.). These methods allow for fast and accurate monitoring and AMR detection of TB strains such as H37Rv and MDR derivatives. In an example, a method of monitoring antibiotic and antifungal drug efficacy or resistance (AMR) on bacterial and fungal cell cultures may include generating in real time the acoustic wave impedance and transmission spectral signals in the presence of the bacterial and fungal cell culture within the monitoring system described herein, including the timepoints wherein the antibiotic or the antifungal drug is introduced to the culture.

The method may also include extracting spectral shape evolution data, peak frequency shift data, motional resistance data, and/or motional induction data from the time-frequency signals using a data simulation and modeling technique based upon a Butterworth-Van-Dyke (BVD) lumped-parameter model and the multi-layer acoustic wave transmission line simulation method.

The method may also compare the extracted data (herein collectively called "bio sensor spectral signatures") to a control set of biosensor spectral signatures corresponding to a control culture strain. The comparison can be performed with a data analysis software package.

The methods and the monitoring system described in various illustrated embodiments disclosed in this patent document can be used for studying drug efficacy and drug resistance are provided. For example, the cells being monitored are drug sensitive and drug resistant pathogenic bacterial strains such as *Mycobacterium tuberculosis* (TB) and/or multidrug resistant *Staphylococcus aureus* (MRSA), and the drug being introduced in the cell culture is an antipathogenic bacterial drug such as an anti-TB drug or methicillin.

In another example, the monitoring system can provide a diagnostic tool for detecting resistance to anti-TB and anti-pathogenic drugs for rapid and high throughput methods or assays for drug discovery and development aimed at mitigating the pathogenic spread of drug resistant TB. In another example, the bacterial culture contains *E. coli*, and using the methods in the illustrated embodiments disclosed in this patent document can readily determine the bacteriostatic effects and bactericidal effects of various agents (e.g. ampicillin and tetracycline).

The methods and the monitoring system described in various illustrated embodiments disclosed in this patent document can be used for studying various fungal strains and the response to fungi-static effects and/or fungicidal effects of anti-fungal agents (e.g. miconazole and amphotericin). For example, the cells being monitored can be drug sensitive and drug resistant strains of pathogenic fungi such as *Candida albicans*, and the drug being introduced in the cell culture is an antifungal such as amphotericin. Similarly, the cells being monitored can be freshly isolated cancer cells, and the agent being introduced in the cell culture is an anti-cancer agent or drug. The method described in various embodiments can also be applied to other bacterial and fungal strains especially pathogenic strains, and involve other drug compounds.

The methods and the monitoring system described in various illustrated embodiments disclosed in the patent document can also be used for studying the growth, drug efficacy and drug resistance in other bacterial strains such as *P. aeruginosa, S. epidermidis, M. tuberculosis, S. aureus, A. baumannii, S. fradiae, S. pneumoniae, S. pyogenes, N. meningitidis, E. aerogenes, K. pneumoniae, B. subtilis* and additional pathogenic or nonpathogenic bacterial strains.

In order to detect AMR for a cell or a pathogen, a compound or drug is added to the cell-growth well, before or during the culturing of the cell or the pathogen. A resistant strain will continue to proliferate and a sensitive strain will show reduced mass accumulation in comparison with a reference. A reference can be a parallel testing of cell growth without the interference of a compound. The reference may also be known data and statistics recorded in a database. The methods and the monitoring system described in various illustrated embodiments disclosed in this patent document enable fast and continuous detection of AMR effects after introducing an agent. For example, accurate detection of AMR can be achieved in 30 minutes for *E. coli*, and in 60 minutes for the yeast, after an agent (e.g. a specific drug) is introduced to the cell culture well.

In addition to the detection of AMR, the method described herein can also be used in the detection of the growth of mammalian cells. For example, the growth of freshly isolated cancer cells and cells from established cancer cell lines can be monitored with an $MZO_{nano}$-QCM based device. Further, the efficacy of a compound in inhibiting the cancer cell growth can be detected without extensive cell culturing.

The $MZO_{nano}$-BAW sensors and associated systems described above can be used to dynamically monitor the samples which are collected from a subject suspected of carrying bacterial pathogens. The subject can be human or animal. The samples may also be collected from a source including food, agricultural products, water supplies, and environment pollution.

In an illustrated embodiment, a method of high-throughput screening of drug compounds (antibiotics, antifungal or chemotherapeutic agents as non-limiting examples) is provided to determine their efficacy in the treatment of various diseases. For example, multiple compounds may be screened by installation of multiple $MZO_{nano}$-BAW sensors (in this case, the $MZO_{nano}$-QCMs) in multiple sample wells. In another example, a large number of compounds may be screened by arraying the unit sensors (in this case, the MZOnano-TFBAR) on a chip, then put it into the sample wells. Examples of the cell target include bacteria, fungi, parasites, and cancer cells. For example, the cell population may include acute lymphoblastic leukemia (ALL), acute myeloid leukemia (AML), chronic lymphocytic leukemia (CLL), chronic myeloid leukemia (CML) or lymphomas.

The method described herein can also be employed in the design and development of personalized disease diagnostics, monitoring, and treatment. For example, various compounds or drugs can be screened against freshly isolated cancer cells to identify the most effective agent. Further, combinations of different compounds or drugs can be examined to develop new treatment regimen.

EXAMPLES

The first two examples using the magnesium-doped zinc oxide (MZO) nanostructures ($MZO_{nano}$) modified bulk acoustic wave (BAW) sensor device ($MZO_{nano}$-BAW), where the Mg composition x in MZO is in the range of $0.04 \leq x \leq 0.05$, and the method of monitoring response of a cell population to an agent, are further provided.

Figure 1B:
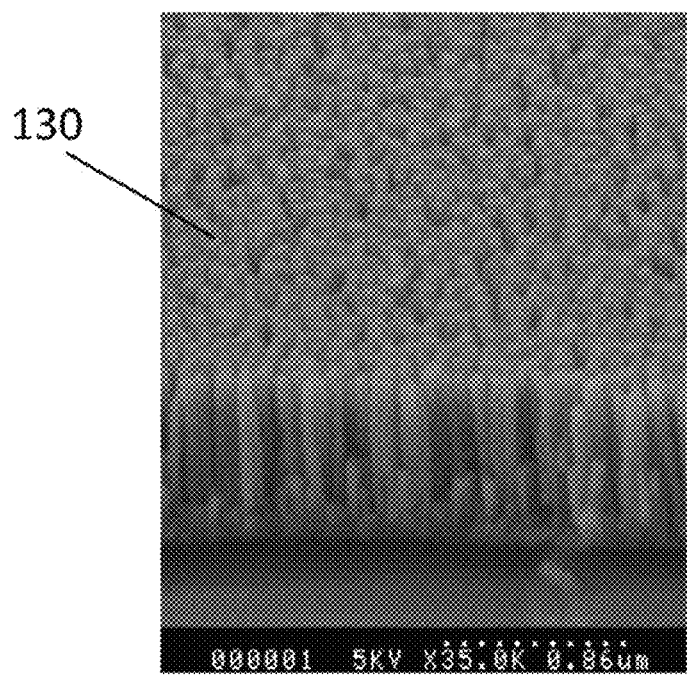
FIG. 1B illustrates the MZO nanostructures deposited on the top of Au electrode surface according to an embodiment.

The first example illustrates the application of a magnesium zinc oxide (MZO) nanostructure-modified quartz crystal microbalance ($MZO_{nano}$-QCM) biosensor disclosed in this document with reference to FIGS. 1A and 1B to dynamically monitor antibiotic effects on sensitive and resistant *E. coli* cells. MZO-nanostructures were grown on a standard QCM top-electrode using metal-organic chemical-vapor deposition. ZnO and MZO nanostructured-films are chosen for their multi-functionality and biocompatibility. Their surface-wettability and morphology can be controlled, offering high-sensitivity to various biological/biochemical species. MZO can withstand a larger pH range than ZnO does. Combining advantages of MZO nanostructures with the dynamic impedance spectrum capability of QCM makes $MZO_{nano}$-QCM a highly-sensitive dynamic biosensor well-suited for AMR detection. The growth of *E. coli* on ZnO and MZO nanostructures was determined by 90-minute incubation. Results show significantly more favorable bacterial growth on MZO (FIG. 2B) compared to ZnO (FIG. 2A).

Figure 4A:
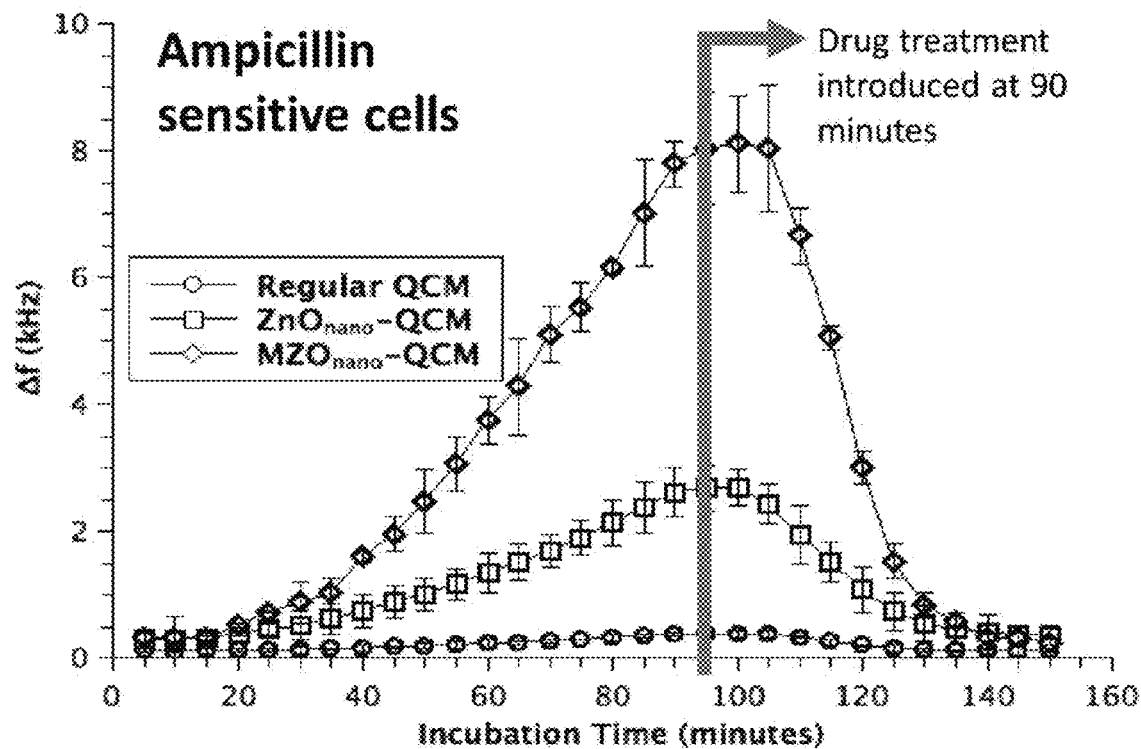
FIGS. 4A-4D illustrate the sensor response on antibiotic effects on E. coli using regular QCM, $ZnO_{nano}$-QCM and $MZO_{nano}$-QCM according to various embodiments.
Figure 4B:
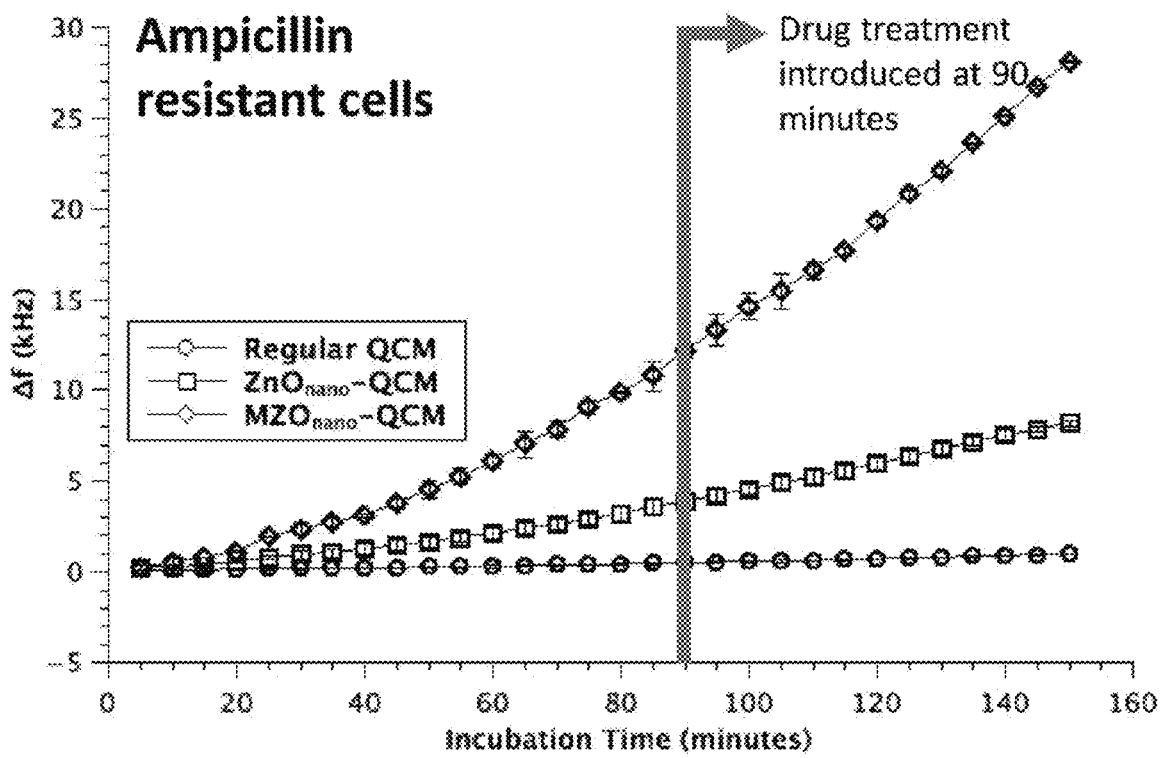
Figure 4C:
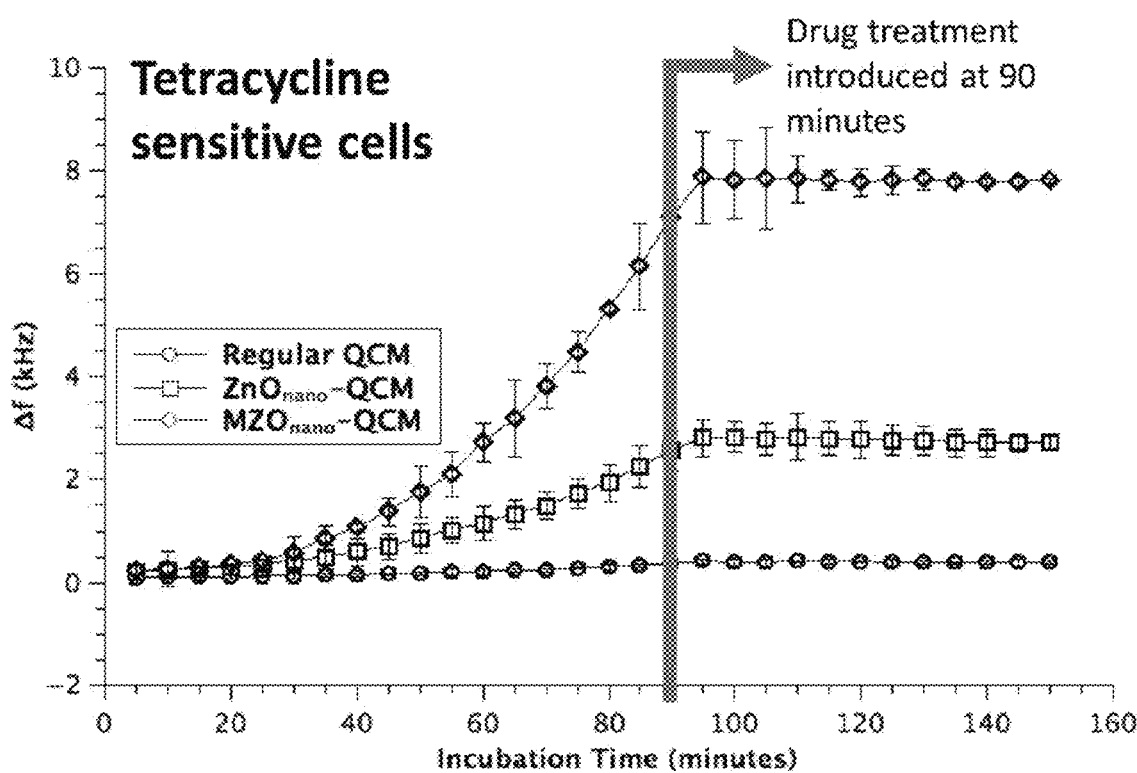
Figure 4D:
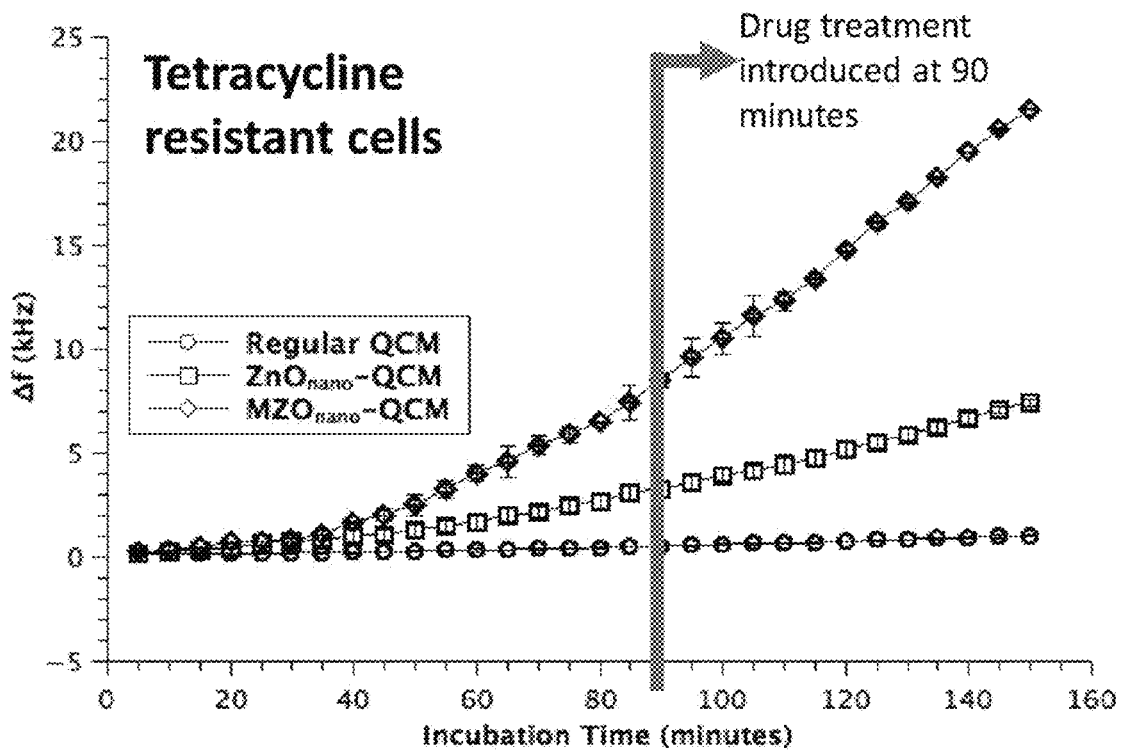
Figure 5A:
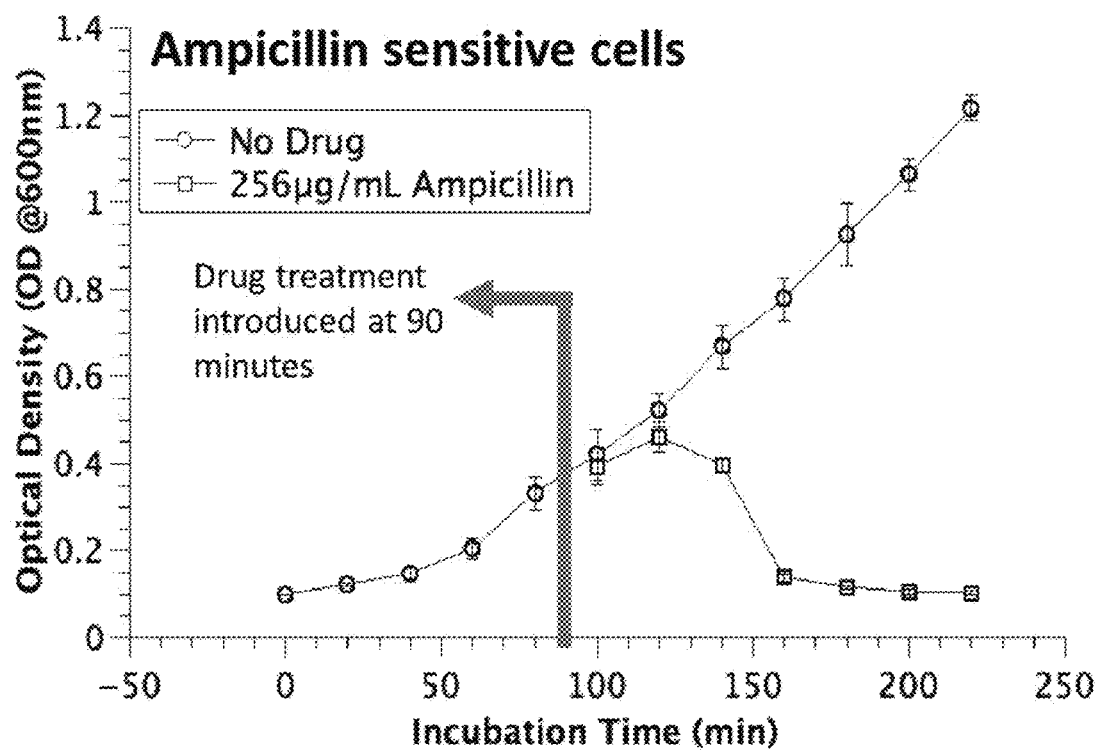
FIGS. 5A-5D illustrate the detection of antibiotic effects on E. coli being verified by the spectrophotometry ($OD_{600}$), which is the currently used AMR detecting technology.
Figure 5B:
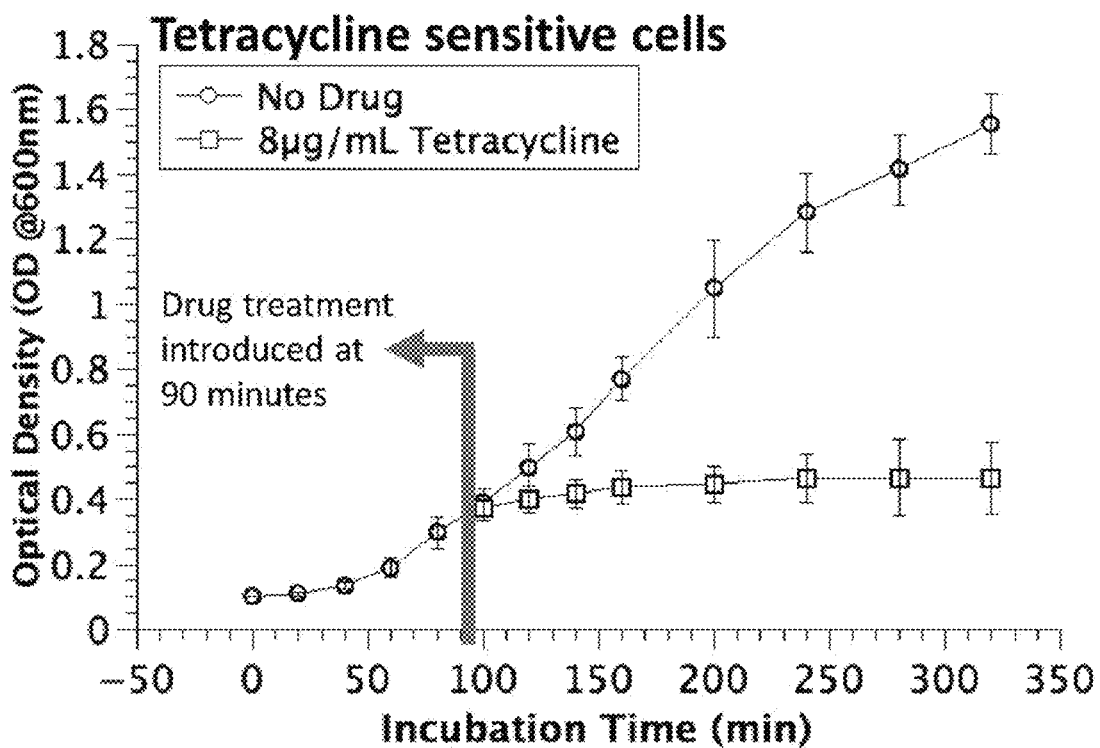
Figure 5C:
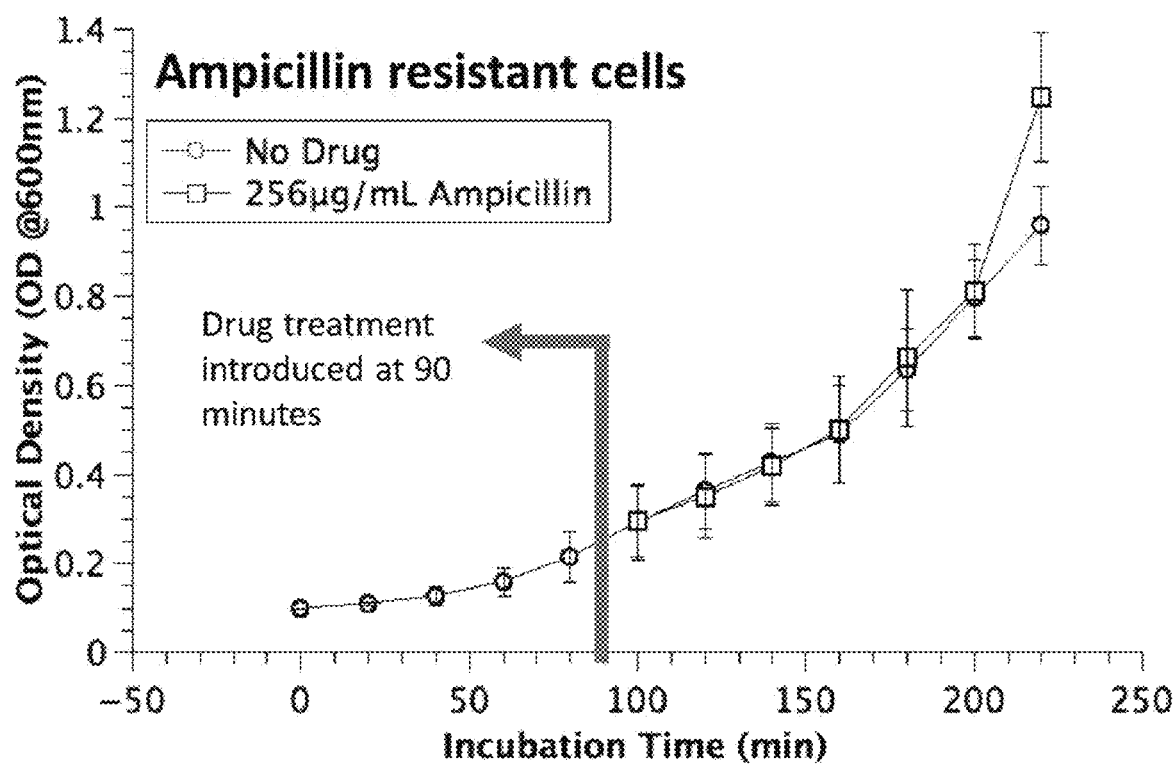
Figure 5D:
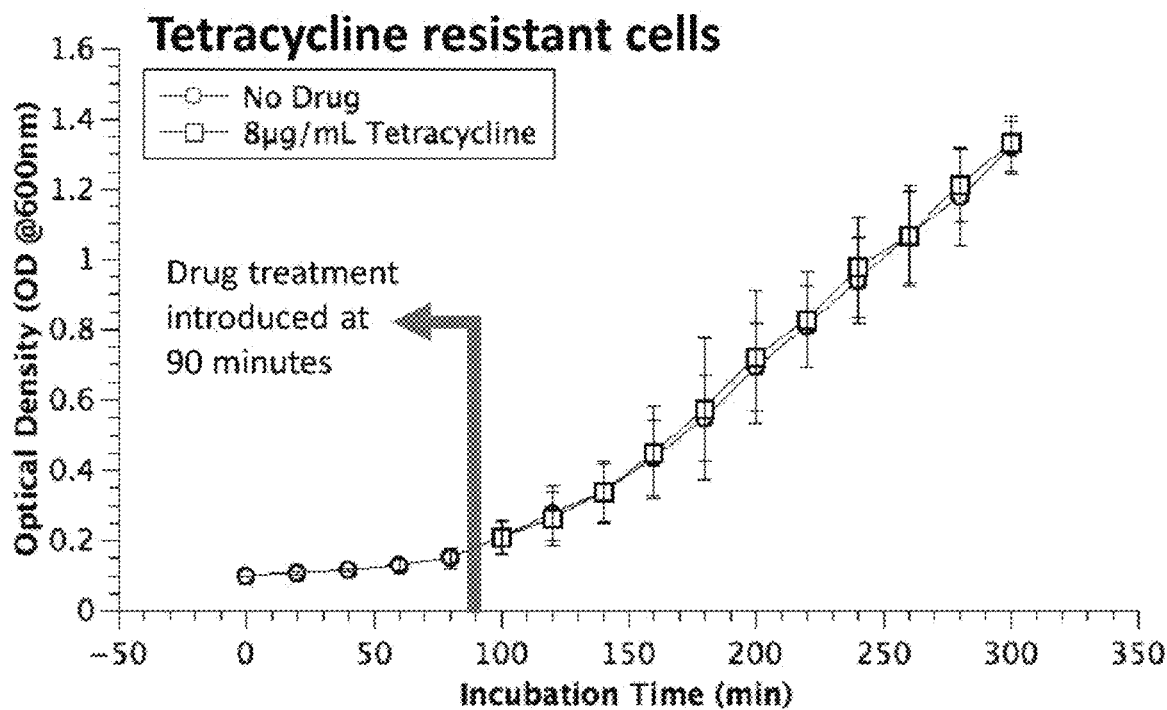

FIGS. 4A-4D show the detection of antibiotic effects on *E. coli* using regular QCM, $ZnO_{nano}$-QCM and $MZO_{nano}$-QCM. The regular QCM failed detection due to low sensitivity while both $ZnO_{nano}$- and $MZO_{nano}$-QCM enable accurate detection of bacterial count during active growth though frequency shifts ($\Delta f$). The $MZO_{nano}$-QCM offered four-fold higher sensitivity than $ZnO_{nano}$-QCM. Antibiotic susceptibility and resistance detections were conducted by treating paired antibiotic-sensitive and resistant *E. coli* with the bactericidal ampicillin (256 µg/mL) and the bacteriostatic tetracycline (8 µg/mL). For ampicillin-sensitive cells (FIG. 4A), $\Delta f$ stopped increasing within 5 min and declined within 10 min upon ampicillin treatment, while $\Delta f$ continued increasing with ampicillin-resistant cells (FIG. 4B). Bacteriostatic effect was exhibited on tetracycline-sensitive cells though flattened signal output upon antibiotic treatment but not on tetracycline-resistant cells (FIGS. 4C-4D). These results were verified by the spectrophotometry ($OD_{600}$) results (FIGS. 5A-D) that exhibited same trends as $MZO_{nano}$-QCM (FIGS. 4A-4D). However, spectrophotometry requires dispensing of samples into vials for placement inside the machine. This also involves time-consuming sample-extraction and measurement, and a much larger sample size. The AMR and drug efficacy detection using the embodiments illustrated in FIGS. 4A-4D do not require sample dispensing nor culture disturbance, and demonstrate rapid, sensitive and real-time AMR detection, promising for diagnosis of microbial pathogens.

The second example demonstrated the application of the same $MZO_{nano}$-QCM biosensor to monitor the effects of amphotericin and miconazole on yeast cells. With reference to FIGS. 6A-6D, comparison of the detection results using various embodiments disclosed in this patent document and the spectrophotometry method shows that the $OD_{600}$ method fails to detect cell-killing effects, and incorrectly identifies amphotericin as a fungi-static drug instead of fungicidal. The result using various embodiments in this patent document accurately detects both drug effects in a rapid manner.

Figure 6A:
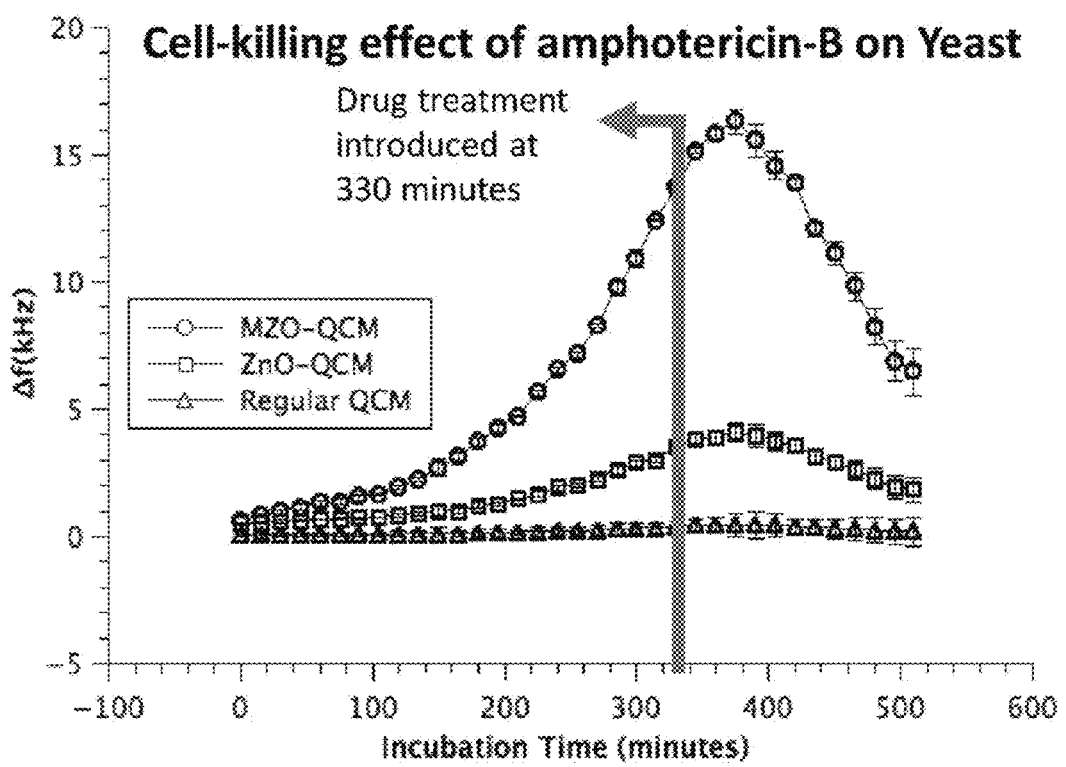
FIGS. 6A-6D illustrate the detection of antifungal drug effects on S. cerevisiae (yeast) using $ZnO_{nano}$-QCM and $MZO_{nano}$-QCM according to various embodiments.
Figure 6B:
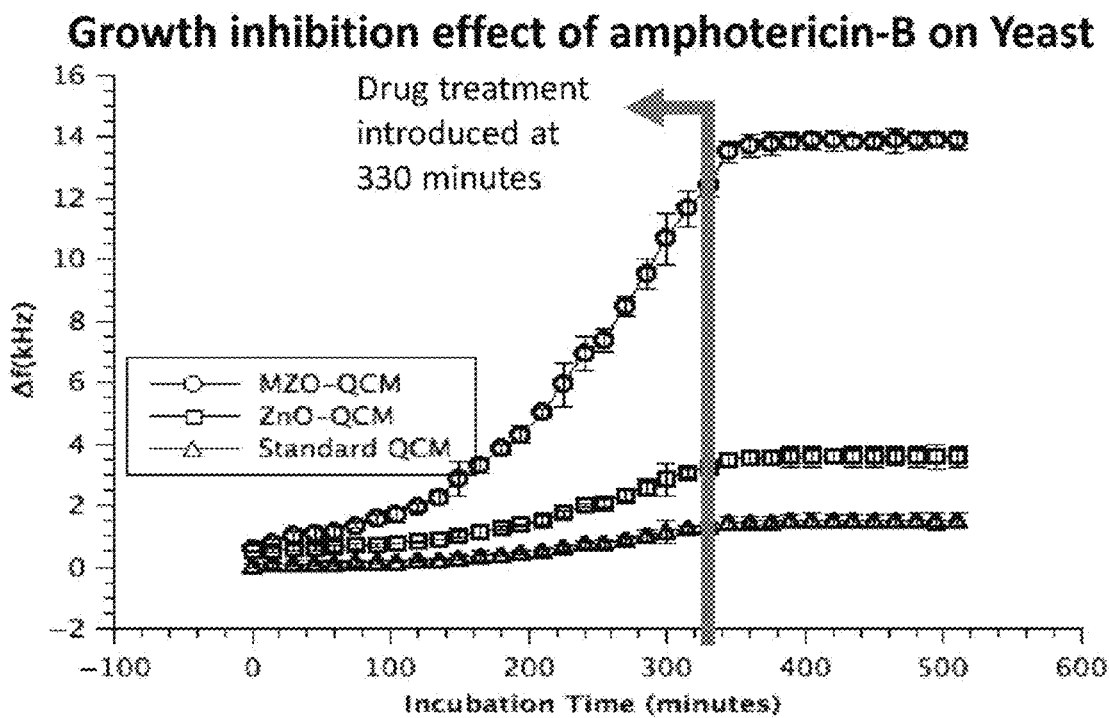
Figure 6C:
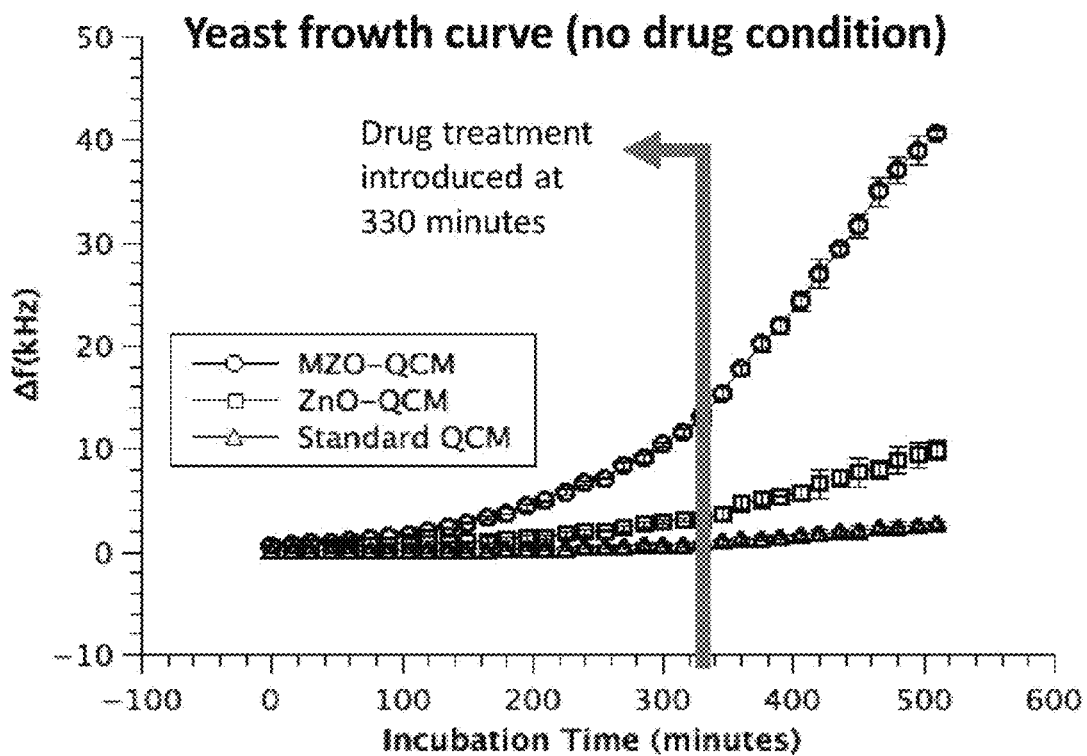
Figure 6D:
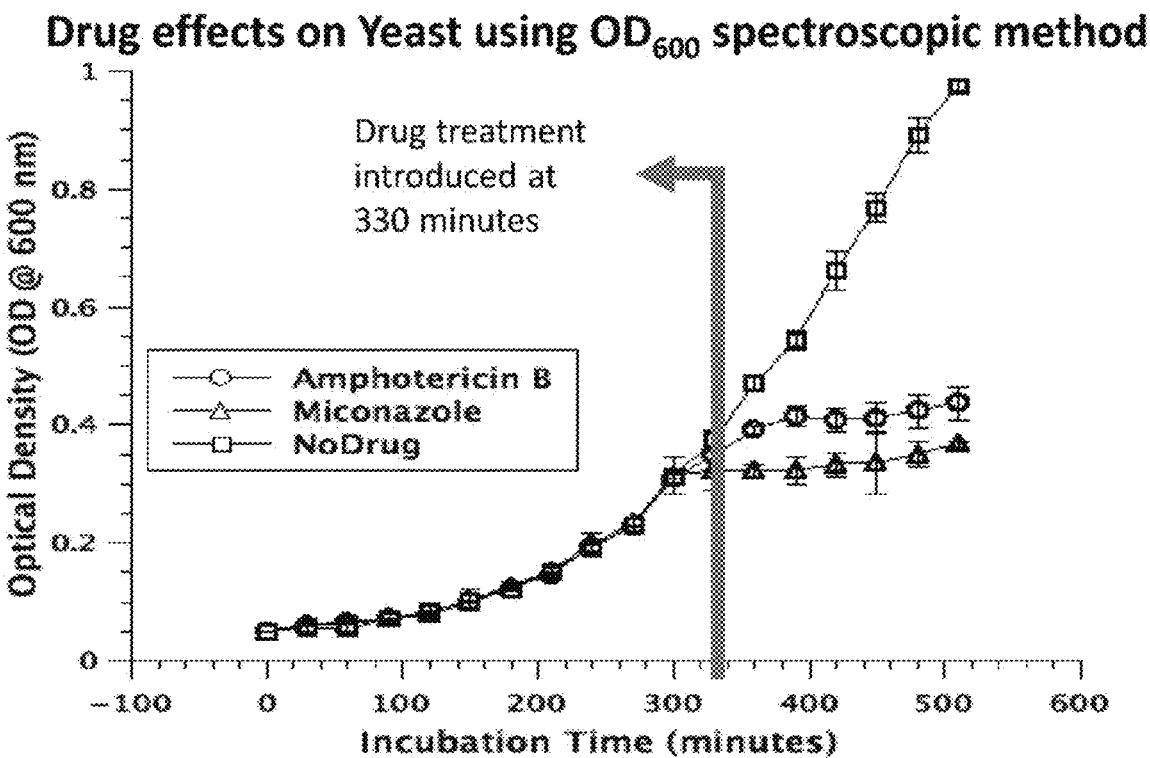

Particularly, FIG. 6A shows the detection of cell-killing effects of amphotericin and growth inhibition effects of miconazole (FIG. 6B) on yeast using $ZnO_{nano}$-QCM and $MZO_{nano}$-QCM. FIG. 6C shows the yeast growth curve without a drug as control. Both amphotericin and miconazole were introduced into the cell cultures at 330 min after initial growth seeding, and the $MZO_{nano}$-QCM has shown both the cell killing and growth inhibition effects within 1 hour of drug treatment. $MZO_{nano}$-QCM also shows 4× higher signal sensitivity compared to the $ZnO_{nano}$-QCM. These results were compared to the OD600 spectroscopic monitoring of the yeast cell culture. FIG. 6D shows the OD600 plots for the antifungal effects of amphotericin and miconazole as well as the no drug condition. Note that the spectroscopic method failed to differentiate between the cell-killing effect of amphotericin and growth inhibition effect of miconazole on yeast. This is due to the fact that the spectroscopic method relies on light absorption by the suspended cells, and dead yeast cells remain in suspension, thus contributing to the absorption.

The use of *E. coli* and yeast to demonstrate the effectiveness of the method and system described in various embodiments disclosed in this patent document for detection of drug effects is due to the fact that both *E. coli* and yeast are common bacterial and fungal models for the development of antibiotics and antifungal drugs. Moreover, both species are one of the most prevalent pathogens that cause human infections.

The third example uses the drug VP16 (also known as etoposide, an anticancer agent), VP16-sensitive ALL cell line (CEM) and its VP16-resistant derivative cell line (CEM-V1) as a model for monitoring the effect of anticancer agents on the growth of cancer cells using the $MZO_{nano}$-QCM sensor device, where the Mg composition x in MZO is 0.03.

Figure 7:
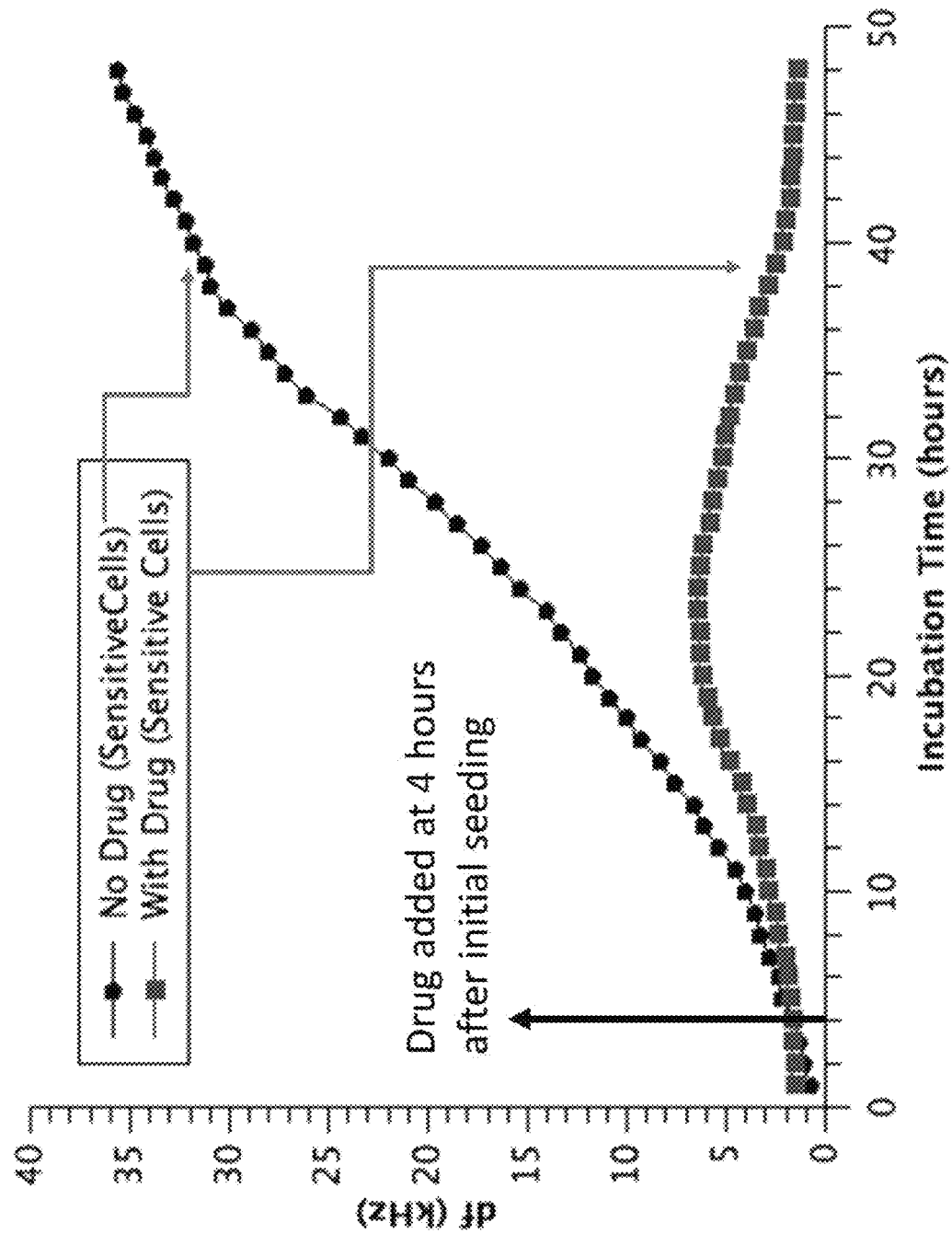
FIG. 7 illustrates the time-dependent frequency shift of the sensor for the entire 48-hour monitoring period of the drug sensitive Acute Lymphoblastic Leukemia (ALL) (CEM) cells for both with and without drug (VP16) treatment cases according to an embodiment.

For all of the experiments in this example, an initial seeding density of $4 \times 10^5$ cells in 2 mL of medium is used, the leukemia cell growth using the $MZO_{nano}$-QCM is monitored dynamically for 48 hours. The drug (VP16) was introduced into the cell culture after 4 hours after the initial seeding. With reference to FIG. 7, the time-dependent frequency shift of the sensor for the entire 48-hour monitoring period of the drug sensitive CEM cells is shown. In the no-drug case, the frequency shift increases exponentially from 0-40 hours (indicating exponential cell accumulation on the sensing area) and then the frequency shift rate decreases showing saturation of the cell growth. In the case where the drug is introduced into the cell culture in the device, it is observed that the cells continue to grow after the drug has been introduced (4 hours after initial seeding), however, it is seen that the drug has taken effect 16 hours after the drug has been introduced. At this point, the cells start to die (or stop to proliferate), as indicated by the decreasing frequency shifts occurring at 20 hours to 48 hours.

Figure 8:
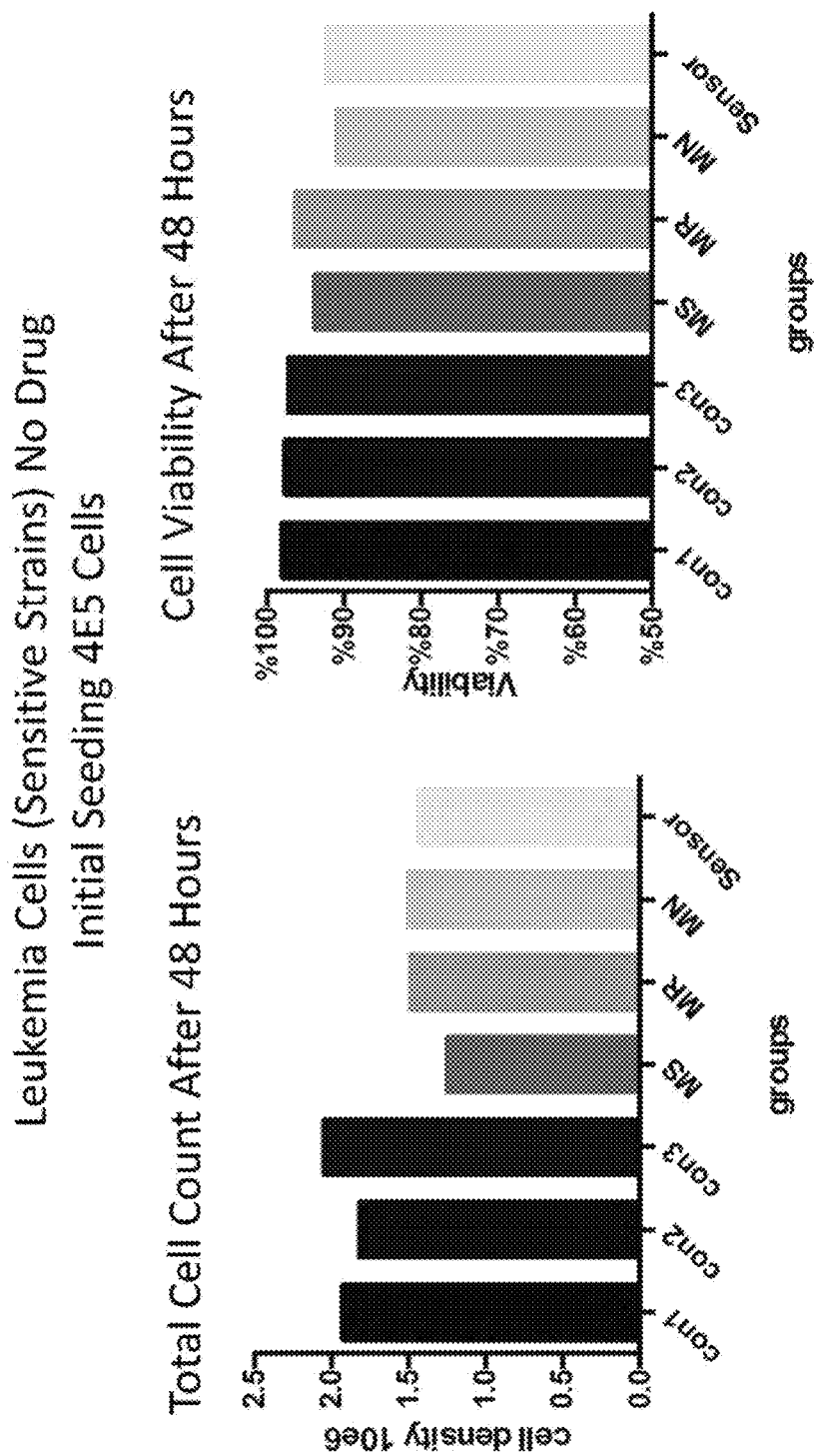
FIG. 8 illustrates the total cell count and cell viability of drug sensitive ALL (CEM) cells without drug treatment in an example.

The sensor measurements can be confirmed using a standard cell viability analyzer (Beckman Coulter, Vi-cell XR) to determine the final cell count and cell viability after 48 hours. In parallel, the same amount of cells in a standard cell well is cultured with the device. At the end of the monitoring cycle (48 hours), 0.5 mL of the cell culture is extracted from the cell well and also from the device. A viability analyzer can be used to do cell counting for the control and cells growing in the device. FIG. 8 (no drug) and FIG. 9 (with drug) show that the total cell count and cell viability match the final signal trend. However, the viability analyzer could not show the real-time effects of the drug treatment on the leukemia cells.

In FIG. 8, the various configurations used in the example include: Con1, con2 and con3 are control cell culture in standard well done in triplicate; MS is control cell culture in standard well with MZO on glass sample (smooth morphology) in bottom; MR is control cell culture in standard well with MZO on glass sample (rough morphology) in bottom; MN is control cell culture in standard well with MZO on glass sample (nano morphology) in bottom; and Sensor is cell culture from the actual MZOnano-QCM sensor+cell well.

Figure 9:
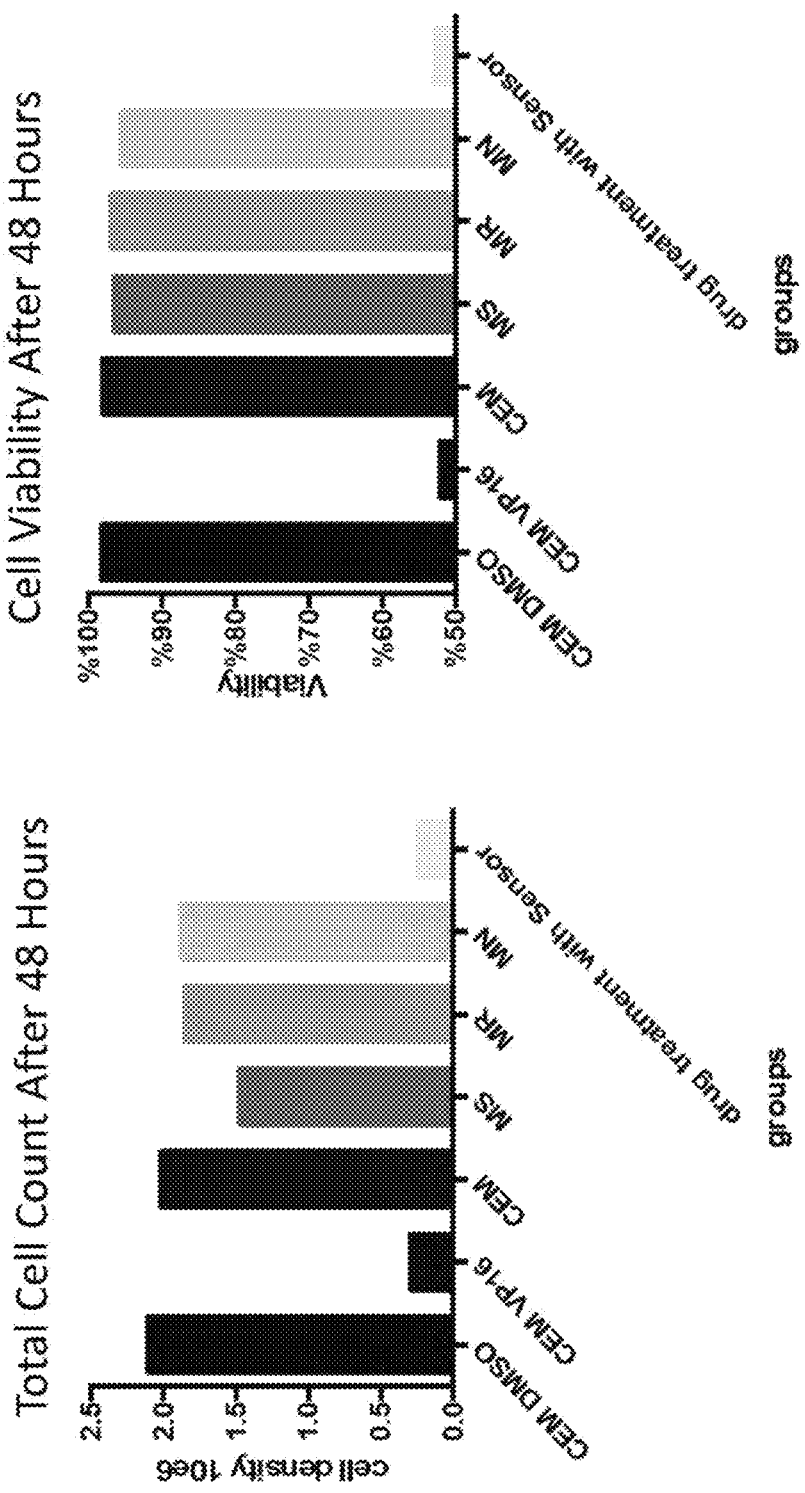
FIG. 9 illustrates the total cell count and cell viability of drug sensitive ALL (CEM) cells with drug treatment in an example.

In FIG. 9, the various configurations used in the example include: CEM DMSO is control cell culture in standard well with DMSO (DMSO was used as drug solvent); CEM VP16 is cell culture in standard well with VP16 drug introduced 4 hours after initial seeding; CEM is control cell culture in standard well; MS is control cell culture in standard well with MZO on glass sample (smooth morphology) in bottom; MR is control cell culture in standard well with MZO on glass sample (rough morphology) in bottom; MN is control cell culture in standard well with MZO on glass sample (nano morphology) in bottom; and Sensor is cell culture from the actual MZOnano-QCM sensor+cell well.

Figure 10:
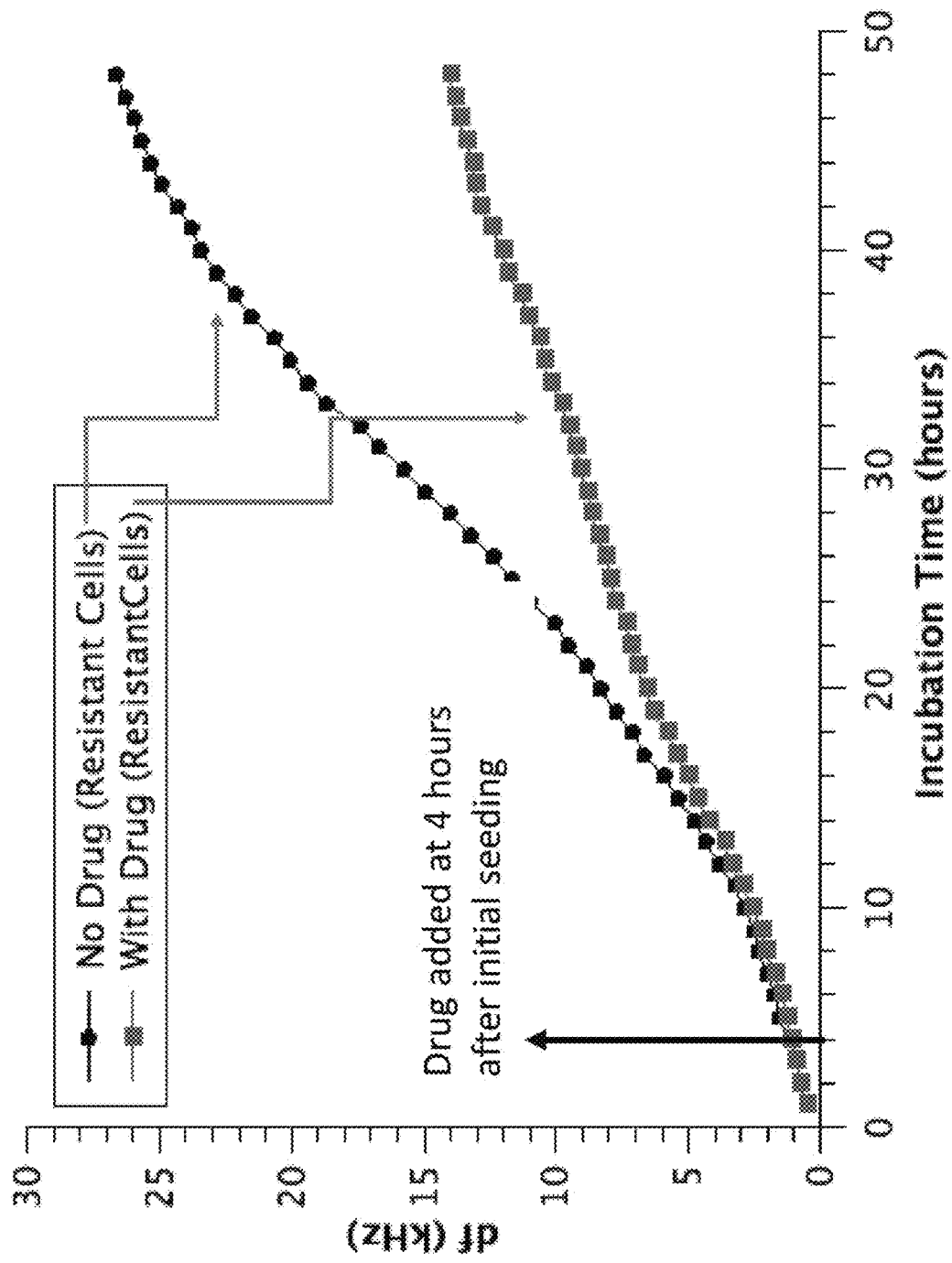
FIG. 10 illustrates the time-dependent frequency shift of the biosensor for the entire 48-hour monitoring period of the drug resistant ALL (CEM-V1) cells in the presence and absence of drug (VP16) treatment in an example.
Figure 11:
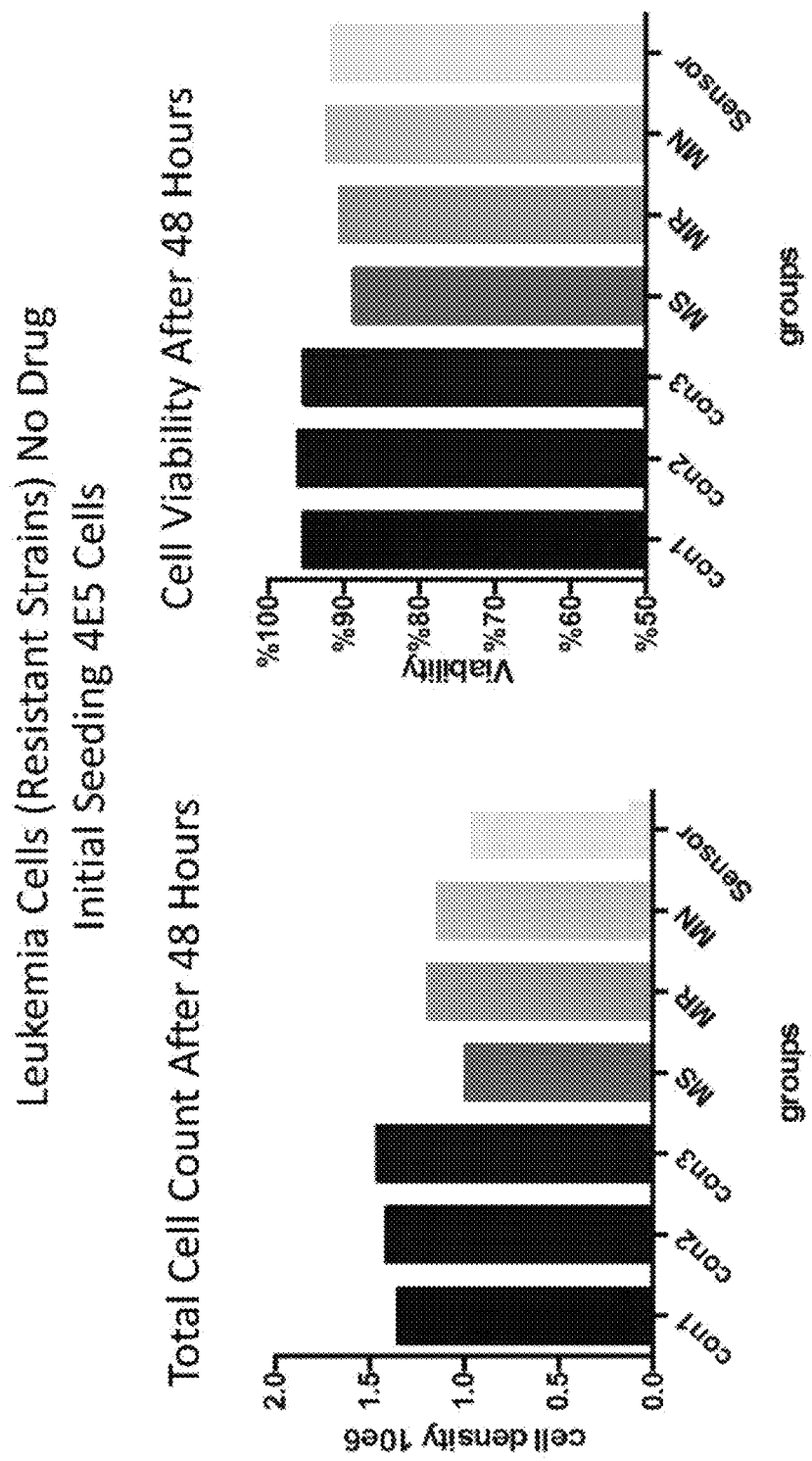
FIG. 11 illustrates the total cell count and cell viability of drug resistant ALL (CEM-V1) cells without drug treatment in an example.
Figure 12:
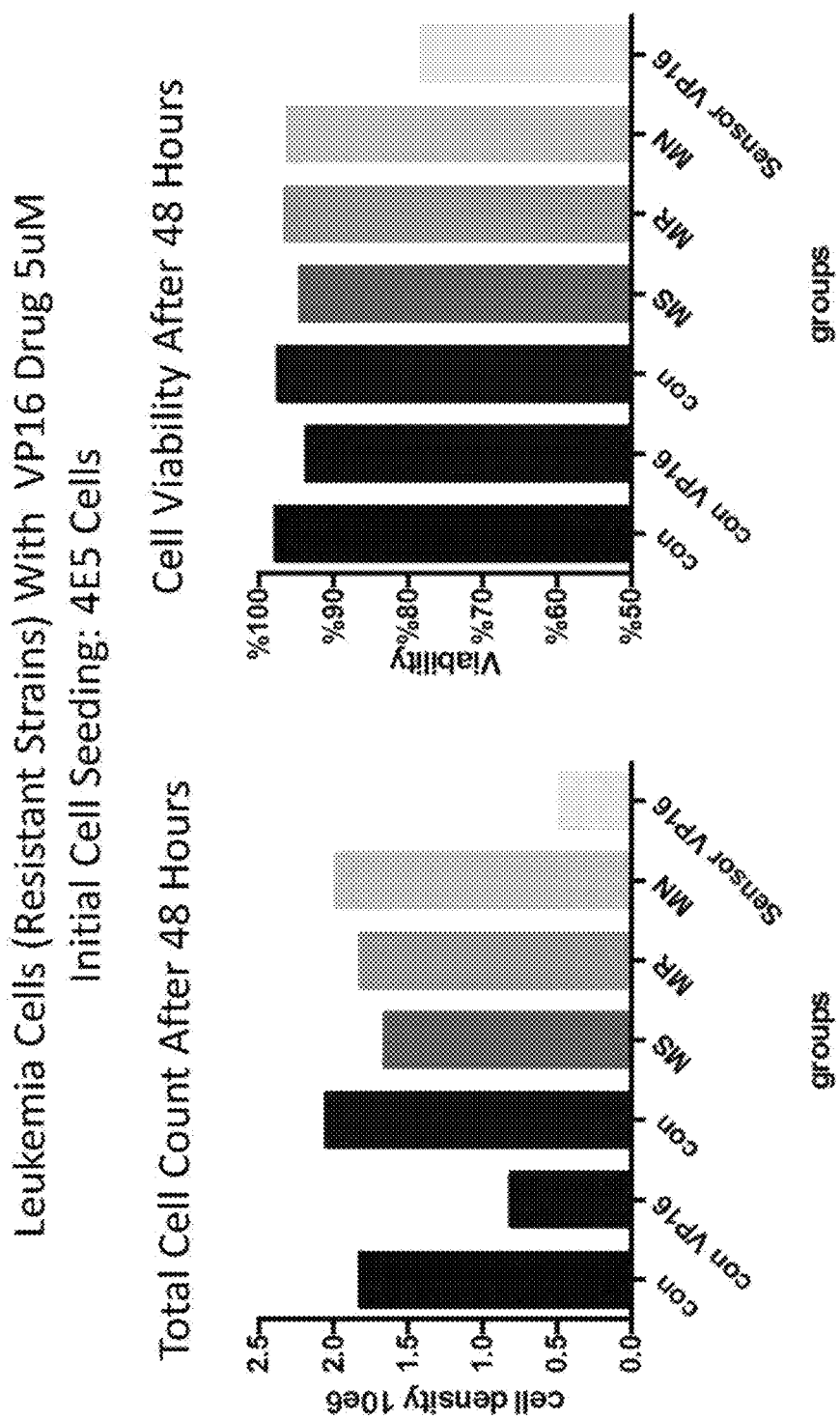
FIG. 12 illustrates the total cell count and cell viability of drug resistant ALL (CEM-V1) cells with drug treatment in an example.

The same experiment can be repeated on drug resistant CEM leukemia cells (CEM-V1) using both the $MZO_{nano}$-QCM sensor and the viability analyzer, and the monitoring can be conducted for 48 hours. FIG. 10 shows the time-dependent frequency shift of the sensor in the presence and absence of drug (VP16) treatment. The drug was added into the cell culture at 4 hours after the initial seeding of $4\times10^5$ cells. It is observed that in the case of the cell culture without drug treatment, the time-dependent frequency shift shows the same trend as in the no-drug case in the sensitive cell experiment. Although at 19 hours after initial seeding (~15 hours after addition of drug), the time-dependent frequency shift started to decrease as compared to that observed in no-drug control, but the continued trend of increase is indicative of continuous cell growth in the presence of the drug. This trend is also confirmed by the cell viability analyzer results which are shown in FIG. 11 and FIG. 12. The various configurations used in the example in FIG. 11 are the same as those described with respect to FIG. 8, and the various configurations used in the example in FIG. 12 are the same as those described with respect to FIG. 9.

Figure 13:
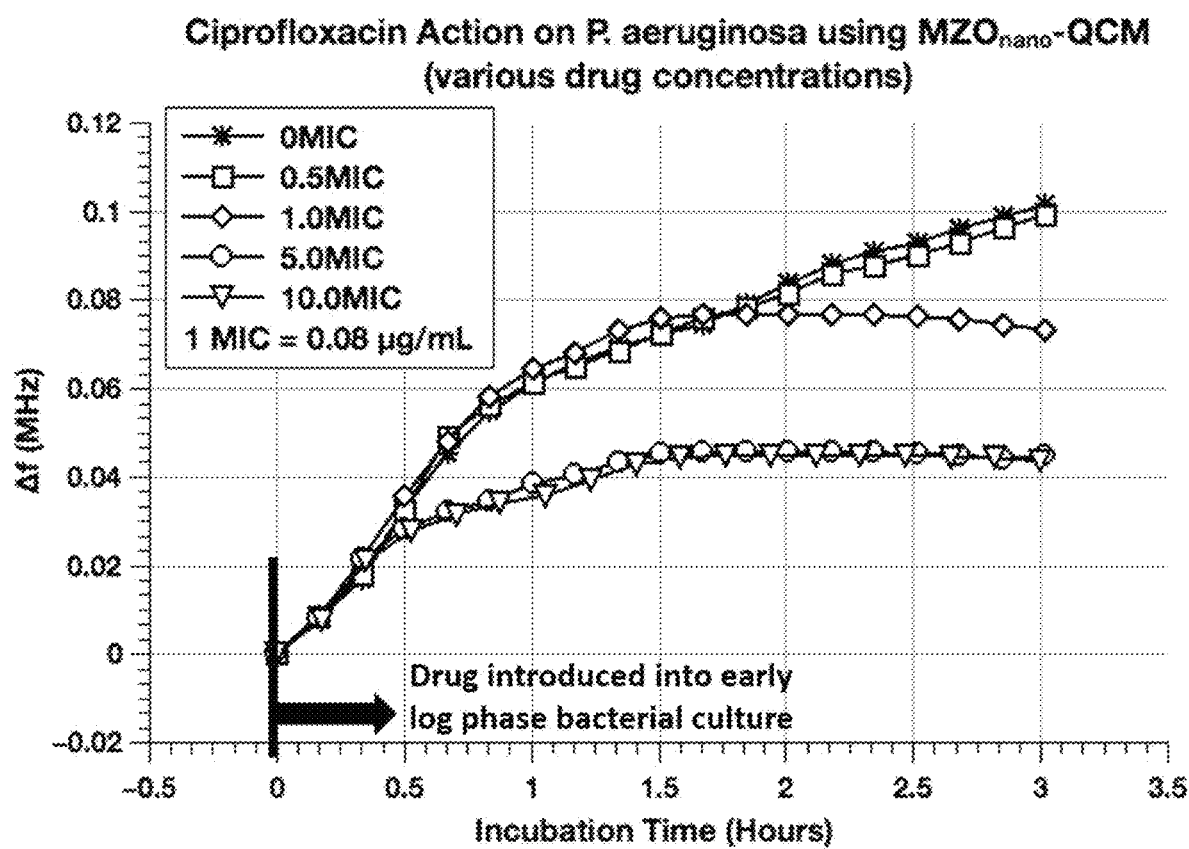
FIG. 13 illustrates the effects of ciprofloxacin on P. aeruginosa for various multiples of the minimum inhibitory concentration (MIC).

FIG. 13 shows the effects of ciprofloxacin on *P. aeruginosa* for various multiples of the minimum inhibitory concentration (MIC). The MIC for ciprofloxacin (0.08 µg/mL) on *P. aeruginosa* was obtained through the standard broth dilution assay. For monitoring the growth of *P. aeruginosa* and the subsequent drug effects using the $MZO_{nano}$-QCM sensor, the sensor was seeded with a 2 mL solution containing a 20-fold diluted *P. aeruginosa* culture under early-log phase and the ciprofloxacin of a particular MIC multiple. The sensor was placed inside an incubator at 37° C. while automatically measuring the acoustic spectrum every 15 minutes for 3 hours. The peak frequency shift (Δf) of the acoustic spectrum was computed and plotted as a function of time. For the no-drug condition (0 MIC), the Δf plot increased continuously for the entire duration of the monitoring period, which corresponds to the mass accumulation of the growing bacteria. A similar pattern was observed for the sample that was treated with 0.5 MIC of ciprofloxacin, which indicates that the drug concentration was not enough to kill the bacteria. At 1 MIC, the plot started to taper off and flatten at 1.5 hours, which was expected for the dosage of exactly at the minimum inhibitory concentration. However, as the drug concentration introduced to the sample reached 5 MIC and 10 MIC, the bacteria grew slightly but never reached the same level as the no-drug Δf values, which indicates that the antibiotic dosage was working to kill the bacteria.

Figure 14:
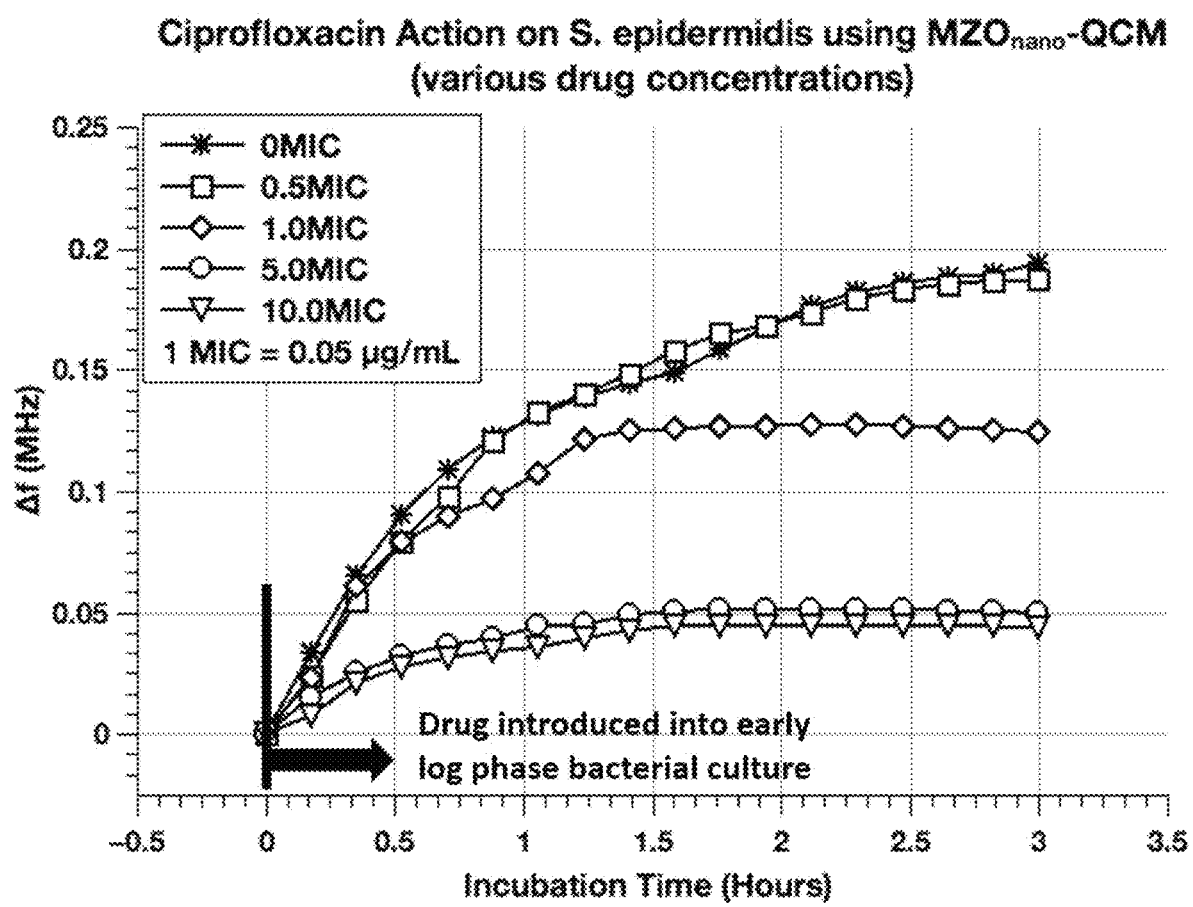
FIG. 14 illustrates the effects of ciprofloxacin on S. epidermidis for various multiples of the minimum inhibitory concentration (MIC).

FIG. 14 shows the effects of ciprofloxacin on *S. epidermidis* for various multiples of the minimum inhibitory concentration (MIC). The MIC for ciprofloxacin (0.05 µg/mL) on *S. epidermidis* was obtained through the standard broth dilution assay. Similar to that of *P. aeruginosa* in FIG. 1, for monitoring the growth of *S. epidermidis* and the subsequent drug effects using the $MZO_{nano}$-QCM sensor, the sensor was seeded with a 2 mL solution containing a 20-fold diluted *S. epidermidis* culture under early-log phase and the ciprofloxacin of a particular MIC multiple. The sensor was placed inside an incubator at 37° C. while automatically measuring the acoustic spectrum every 15 minutes for 3 hours. The peak frequency shift (Δf) of the acoustic spectrum was computed and plotted as a function of time Similar to the conditions in FIG. 1, for the no-drug condition (0 MIC), the Δf plot increased continuously for the entire duration of the monitoring period, which corresponds to the mass accumulation of the growing bacteria. The same observation was obtained for the 0.5 MIC ciprofloxacin treatment, which indicates that the drug concentration was not enough to kill the bacteria. At 1 MIC, the plot started to taper off and flatten at 1 hour indicative of the behaviour of the cells under minimum inhibitory concentration. For the cases of 5 MIC and 10 MIC dosages, the bacteria grew slightly but never reached the same level as the no-drug Δf values, which indicates that the antibiotic dosage was working to kill the bacteria.

Figure 15A:
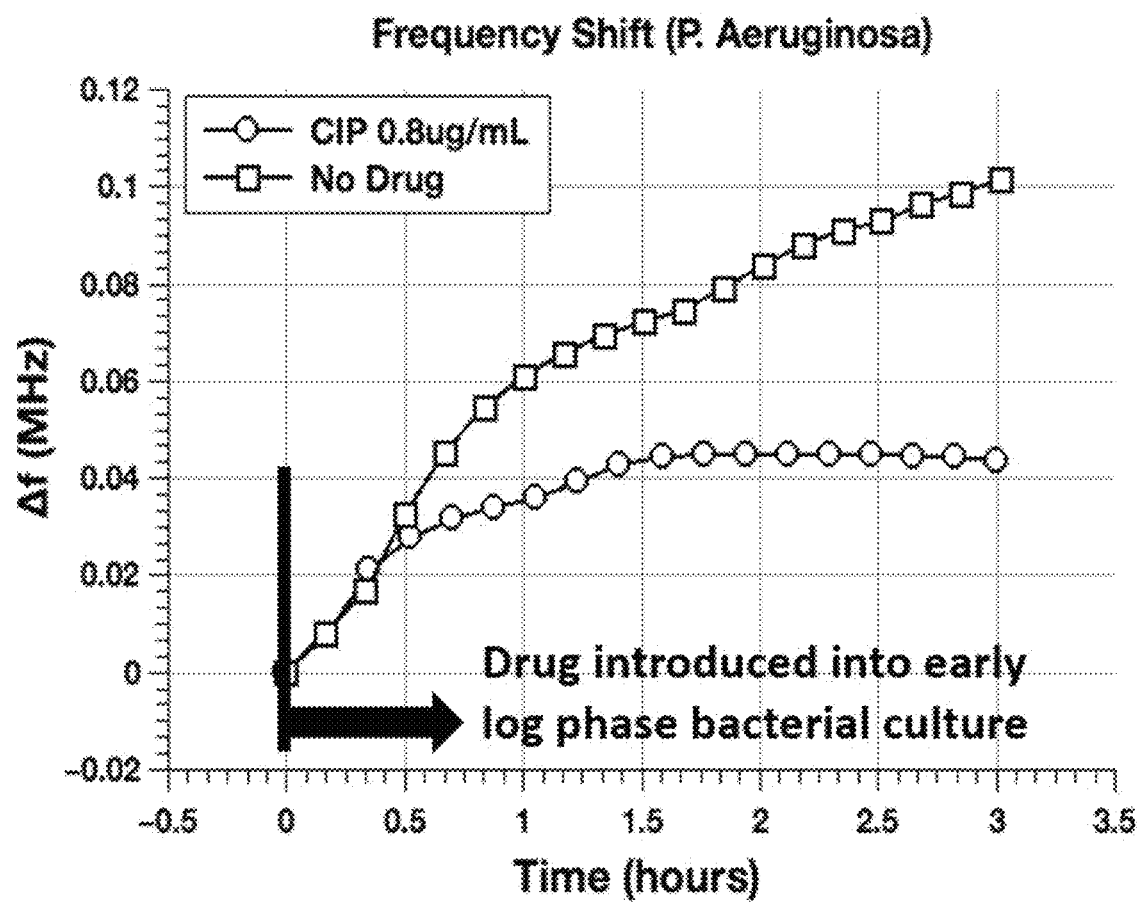
FIGS. 15(a) and 15(b) illustrate two principal signals from the sensor, which provide multiple parameters that relate to biophysical properties of the bacterial strain culture.
Figure 15B:
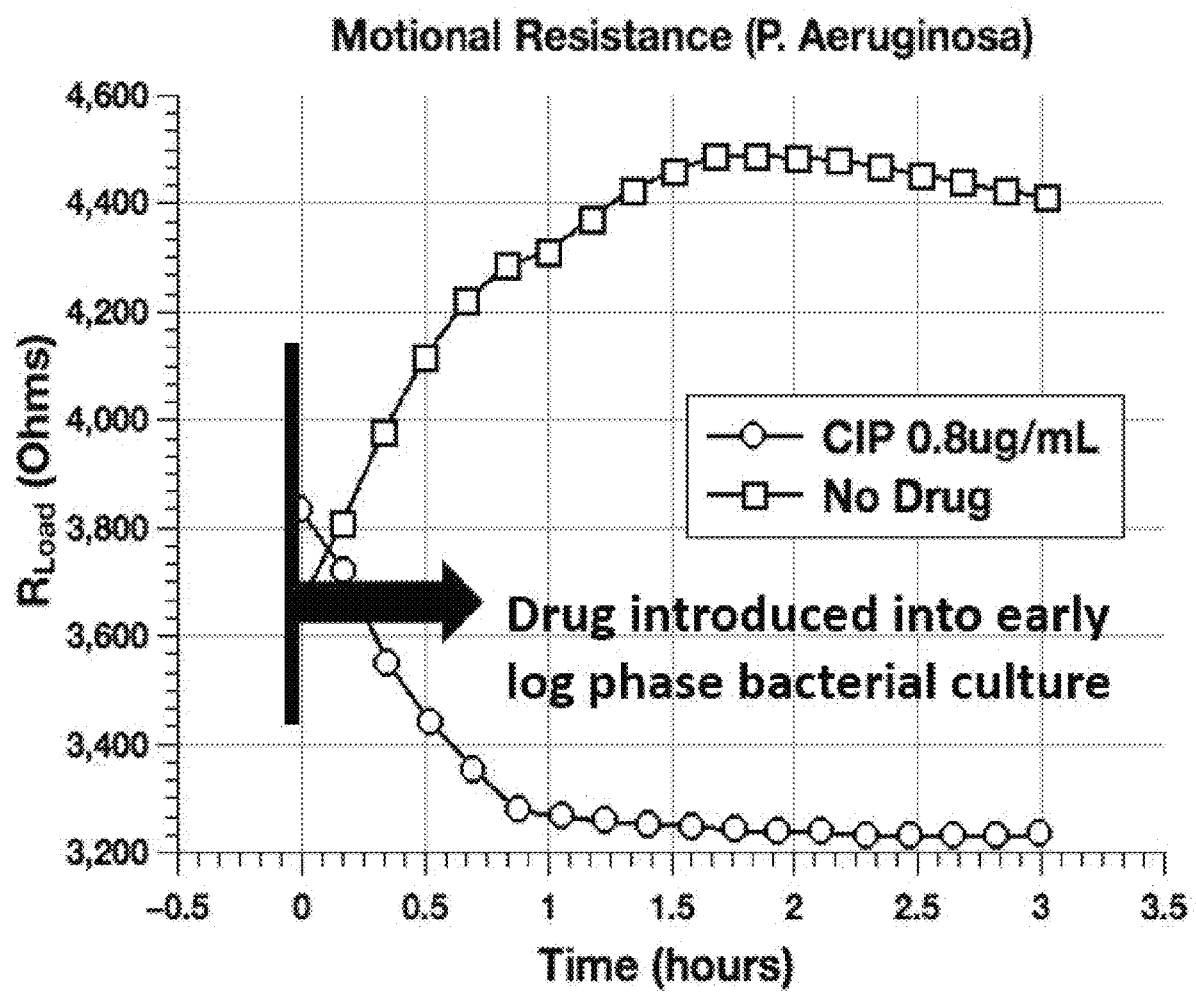

Two principal signals from the sensor provide multiple parameters that relate to biophysical properties of the bacterial strain culture: the frequency shift and the acoustic impedance. Both parameters are obtained from the sensor's transmission admittance spectrum ($Y_{21}$) signal. The frequency shift (FIG. 15(*a*)) of the peaks of the admittance spectrum is directly proportional to the mass accumulation on the sensor. The acoustic impedance is obtained from the amplitude and shape of the admittance spectrum and is a complex quantity (it has a real and imaginary component). The real component of the acoustic impedance is the motional resistance (FIG. 15(*b*)) which is directly calculated from the admittance spectrum using the Butterworth Van Dyck Model (BVD) indicates cell stiffness and elasticity (viscoelastic transitions of the cell culture). The viscoelastic transition monitoring is especially important in determining whether the sample in the sensor system is forming a normal cell culture or experiencing biomechanical disintegration due to drug effects on either the cell wall or the chromosomal DNA. These two signals are readily available from the sensor upon its measurement of the admittance spectrum. The motional resistance complements the information provided by the frequency shift plot. FIG. 15(*b*) shows that the motional resistance determined for *P. aeruginosa* cultured on the sensor in the presence or absence of ciprofloxacin (CIP) is dramatically different.

The above-disclosed systems, methods and features, as well as alternatives, may be combined into many other different systems, methods or applications. Various presently unforeseen or unanticipated alternatives, modifications, variations or improvements may be made by those skilled in the art, each of which is also intended to be encompassed by the disclosed embodiments.

The invention claimed is:

1. A method of monitoring response of a cell population to an agent, comprising:
   providing a magnesium-doped zinc oxide (MZO) nanostructures ($MZO_{nano}$) modified bulk acoustic wave (BAW) sensor device ($MZO_{nano}$ BAW) comprising:
   a piezoelectric layer sandwiched between a top and bottom electrodes, and
   $Mg_xZn_{1-x}O$ (MZO)-based nanostructures deposited and patterned on a top surface of the top electrode, wherein the Mg composition x in MZO is in the range of 0<x<0.2;
   culturing a cell population in contact with said nanostructures;
   contacting the cell population with an agent;
   continuing to culture the cell population;

generate the time-frequency signals and receive the output signals corresponding to frequency response spectra from said MZO$_{nano}$-BAW sensor device;
dynamically and continuously monitoring changes in the output signals by measuring the frequency response spectra; and
extracting data from the output signals from said MZO$_{nano}$-BAW sensor device, and analyzing the data to determine a response of said cell population to said agent.

2. The method of claim 1, wherein said extracted data comprises one or more of spectral shape evolution data, peak frequency shift data, motional resistance data, and motional induction data derived from a modeling technique based upon a Butterworth-Van-Dyke (BVD) lumped-parameter model.

3. The method of claim 1, wherein said agent is antimicrobial or antibiotic and the method further comprises comparing said extracted data with a reference to determine the anti-microbial effect of said agent and/or antibiotic resistance of said cell population to said agent.

4. The method of claim 1, wherein said agent is anticancer and the method further comprises comparing said extracted data with a reference to determine the anti-cancer effect of said agent.

5. The method of claim 1, wherein said cell population comprises bacterial cells, fungal cells, parasite cells, or cancer cells.

6. The method of claim 5, wherein said cell population comprises acute lymphoblastic leukemia (ALL), acute myeloid leukemia (AML), chronic lymphocytic leukemia (CLL), chronic myeloid leukemia (CML) or lymphomas.

7. The method of claim 1, wherein said cell population comprises a pathogenic bacterial cell selected from the group consisting of *P. aeruginosa*, *S. epidermidis*, *A. baumannii*, *S. fradiae*, *S. pneumoniae*, *S. pyogenes*, *N. meningitidis*, *E. aerogenes*, *K. pneumoniae*, *B. subtilis*, *M. tuberculosis*, and *S. aureus*, and said agent is an antibiotics.

8. The method of claim 7, wherein said cell population comprises a drug-resistant bacterial cell selected from the group consisting of *M. tuberculosis* (TB) and methicillin-resistant *S. aureus* (MRSA), and said agent is an anti-pathogenic bacterial agent selected from the group consisting of an anti-TB agent and an anti-MRSA agent.

9. The method of claim 1, wherein said cell population comprises fungal cells selected from the group consisting of *Candida albicans* and *Cryptococcus neoformans*, and said agent is an anti-fungal agent selected from the group consisting of polyenes, azole, allylamines and echinocandins based anti-fungal agents, amphotericin, miconazole, 5-fluorocytosine, griseofulvin, tolnaftate, and ciclopirox.

10. The method of claim 1, wherein said cell population comprises freshly isolated cancer cells, and said agent is an anti-cancer agent.

11. The method of claim 1, wherein the value of x is selected to provide one or more predetermined characteristics of said MZO nanostructures selected from the group consisting of surface morphology, wettability, pH stability range, and toxicity control in order to optimize the sensitivity and selectivity of said MZO$_{nano}$-BAW sensor device.

12. The method of claim 1, wherein said MZO nanostructures comprise a surface morphology selected from the group consisting of substantially flat surface, rough surface, and nanotip or rod arrays, wherein the nanotip or rod arrays comprise nanotips or rods adjacent to each other and have sharp tips or rounded tops to enhance attachment of said cell population to said MZO nanostructure surface.

13. The method of claim 1, wherein the response is the rate of change of cell number in the cell population.

14. The method of claim 1, wherein the agent is selected from the group consisting of ampicillin, tetracycline, and ciprofloxacin.

15. A method of monitoring the growth of a cell population, comprising:
providing a magnesium-doped zinc oxide (MZO) nanostructures (MZO$_{nano}$) modified bulk acoustic wave (BAW) sensor device (MZO$_{nano}$-BAW) comprising:
a piezoelectric layer sandwiched between a top and bottom electrodes, and
Mg$_x$Zn$_{1-x}$O (MZO)-based nanostructures deposited and patterned on a top surface of the top electrode, wherein the Mg composition x in the Mg$_x$Zn$_{1-x}$O is in the range of 0<x<0.2;
culturing a cell population in contact with said nano structures;
collecting output signals corresponding to frequency response spectra of the MZO$_{nano}$-BAW sensor device;
extracting data from the output signals indicative of a change in a viscoelastic property and/or mass-loading of the cells of the cell population, and analyzing the data using simulation and modeling;
wherein said cell population is collected from a subject suspected of carrying bacterial pathogens.

16. The method of claim 1 or claim 15, wherein a plurality of the sensor devices are arrayed on a chip for high throughput measurements and diagnostics, wherein the MZO$_{nano}$-BAW sensor device is
(a) an MZO$_{nano}$-QCM, wherein the said MZO nanostructures are deposited on the surface of the top electrode of the regular QCM (Quartz Crystal Microbalance); or
(b) an MZO$_{nano}$-TFBAR, wherein the said MZO nanostructures are deposited on the surface of the top electrode of the regular TFBAR (Thin Film Balk Acoustic wave Resonator).

17. The method of claim 1, wherein said MZOnano-BAW sensor device is an MZO$_{nano}$-QCM, wherein the said MZO nano structures are deposited on the surface of the top electrode of the regular QCM (Quartz Crystal Microbalance).

18. The method of claim 1, wherein said MZO$_{nano}$-BAW sensor device is the MZO$_{nano}$-TFBAR, wherein the said MZO nano structures are deposited on the surface of the top electrode of the regular TFBAR (Thin Film Balk Acoustic wave Resonator).

19. The method of claim 18, wherein the MZO$_{nano}$-TFBAR device operates at a frequency in GHz or multi-GHz range by properly designing and depositing the thin piezoelectric layer with the proper thickness.

20. A bulk acoustic wave (BAW) sensor device for monitoring growth of a cell population, comprising:
a piezoelectric layer sandwiched between a top and bottom electrodes, each of the top and bottom electrodes being a metal, alloy and/or transparent conductive oxide film that is deposited and patterned on the piezoelectric layer; and
Mg$_x$Zn$_{1-x}$O (MZO)-based nanostructures for culturing the cell population deposited and patterned on a top surface of the top electrode of the BAW device, wherein the Mg composition x in the Mg$_x$Zn$_{1-x}$O is in the range of 0<x<0.2.

21. The sensor device of claim 20, wherein the sensor device is a MZO$_{nano}$-QCM sensor, in which the piezoelectric layer comprises a quartz crystal microbalance (QCM) and said MZO nano structures are deposited on the top surface of the top electrode.

22. The sensor device of claim 21, wherein a plurality of the sensor devices are arrayed on a chip for high throughput measurements and diagnostics.

23. The sensor device of claim 20, wherein the sensor device is a $MZO_{nano}$-TFBAR sensor, in which the piezoelectric layer comprises a thin film balk acoustic wave resonator (TFBAR) and said MZO nano structures are deposited on the top surface of the top electrode.

24. The sensor device of claim 23, wherein the sensor is configured to operate at a frequency in GHz or multi-GHz range to increase the sensitivity by thin piezoelectric layer.

25. The sensor device of claim 23, wherein a plurality of the sensor devices are arrayed on a chip for high throughput measurements and diagnostics.

26. The sensor device of claim 20, wherein the device is configured to operate in dual mode operation comprising measurements of BAW signals and optical signals in fluorescence, either simultaneously or separately, for monitoring antimicrobial resistance.

27. The bulk acoustic wave (BAW) sensor device of claim 20, further comprising at least one of ZnO-based nano structures, $SiO_2$-base nanostructures, $TiO_2$-based nanostructures and silicon nitride-based nanostructures deposited and patterned on the top surface of the top electrode of the BAW device.

* * * * *

UNITED STATES PATENT AND TRADEMARK OFFICE
CERTIFICATE OF CORRECTION

| | | |
|---|---|---|
| PATENT NO. | : 10,801,879 B2 | Page 1 of 1 |
| APPLICATION NO. | : 15/927710 | |
| DATED | : October 13, 2020 | |
| INVENTOR(S) | : Yicheng Lu et al. | |

It is certified that error appears in the above-identified patent and that said Letters Patent is hereby corrected as shown below:

In the Specification

Column 1, Lines 20-27 Delete the Statement Regarding Federally Sponsored Research and replace with:
This invention was made with government support under grant number 1264508 awarded by the National Science Foundation. The government has certain rights in the invention.

Signed and Sealed this
Third Day of October, 2023

Katherine Kelly Vidal
*Director of the United States Patent and Trademark Office*